United States Patent
Li et al.

(10) Patent No.: US 6,235,748 B1
(45) Date of Patent: May 22, 2001

(54) OXO-SUBSTITUTED COMPOUNDS, PROCESS OF MAKING, AND COMPOSITIONS AND METHODS FOR INHIBITING PARP ACTIVITY

(75) Inventors: Jia-He Li, Cockeysville; Jie Zhang, Ellicott City, both of MD (US)

(73) Assignee: Guilford Pharmaceuticals Inc., Baltimore, MD (US)

(*) Notice: Subject to any disclaimer, the term of this patent is extended or adjusted under 35 U.S.C. 154(b) by 0 days.

(21) Appl. No.: 09/524,750

(22) Filed: Mar. 14, 2000

Related U.S. Application Data

(60) Division of application No. 09/079,509, filed on May 15, 1998, now abandoned, which is a continuation-in-part of application No. 08/922,520, filed on Sep. 3, 1997, now abandoned.

(51) Int. Cl.[7] ................... A61K 31/4353; C07D 221/18; C07D 471/02

(52) U.S. Cl. ........................... 514/285; 546/62; 546/70; 428/451; 428/455; 428/464

(58) Field of Search ................... 546/108, 62, 70; 514/285; 428/451, 455, 464; 534/560; 424/451, 463, 464, 474

(56) References Cited

U.S. PATENT DOCUMENTS

| | | |
|---|---|---|
| 3,291,801 | 12/1966 | Montgomery . |
| 3,507,872 | 4/1970 | Hegar . |
| 3,838,134 | 9/1974 | Gauthier . |
| 4,082,741 | 4/1978 | Hunger et al. . |
| 4,169,897 | 10/1979 | Meyer et al. . |
| 4,382,943 | 5/1983 | Winter et al. . |
| 5,177,075 | 1/1993 | Suto et al. . |
| 5,274,097 | 12/1993 | Schohe et al. . |
| 5,587,384 | 12/1996 | Zhang et al. . |
| 5,756,510 | 5/1998 | Griffin et al. . |

FOREIGN PATENT DOCUMENTS

| | | |
|---|---|---|
| WO 99/11622 | 3/1999 | (WO) . |
| WO 99/11623 | 3/1999 | (WO) . |
| WO 99/11628 | 3/1999 | (WO) . |
| WO 99/11644 | 3/1999 | (WO) . |
| WO 99/11645 | 3/1999 | (WO) . |
| WO 99/11649 | 3/1999 | (WO) . |
| WO 99/59973 | 11/1999 | (WO) . |
| WO 99/59975 | 11/1999 | (WO) . |
| WO 00/39070 | 7/2000 | (WO) . |
| WO 00/39104 | 7/2000 | (WO) . |

OTHER PUBLICATIONS

Szabo et al., PNAS 93:1753–58 (1996).
Baer, Journal of Organic Chemistry, 29:11, 3180–85 (1964).
Ochiai, Pharm. Bull., 5:289–91 (1957).

Szabo et al., "Inhibition of poly(ADP–ribose) synthetase attenuates neutrophil recruitment and exerts antiinflammatory effects", J. Exp. Med., 1997, Oct. 6; 186(7): 1041–9.

Suto et al., "Dihydroisoquinolinones: the deisgn and synthesis of a new series of potent inhibitors of poly(ADP–ribose) polymerase", Anti–Cancer Drug Deisgn (1991); 7, 107–117.

Zhang et al., "Nitric Oxide Activation of Poly(ADP–ribose) Synthetase in Neurotoxicity," Science, 263:687–89 (1994).

Wallis et al., "Neuroprotection Against Nitric Oxide Injury with Inhibitors of ADP–ribosylation," NeuroReport, 5:3, 245–48 (1993).

Endres et al., "Ischemic Brain Injury is Mediated by the Activation of Poly(ADP–Ribose) Polymerase," J. Cerebral Flood Flow Metabol., 17(11):1143–51 (1997).

Wallis et al., Traumatic Neuroprotection with Inhibitors of Nitric Oxide and ADP–Ribosylation, Brain Res., 710:169–77 (1996).

Thiemermann et al., "Inhibition of the Activity of Poly (ADP Ribose) Synthetase Reduces Ischemia–Reperfusion Injury in the Heart and Skeletal Muscle", Proc. Natl. Acad. Sci. USA, 94:679–83 (1997).

Zhang et al., "Poly(ADP–Ribose) Synthetase Activation: An Early Indicator of Neurotoxic DNA Damage", J. Neurochem., 65:3, 1411–14 (1995).

Cosi et al., "Poly(ADP–Ribose) Polymerase (PARP) Revisited. A New Role for an Old Enzyme: PARP Involvement in Neurodegeneration and PARP Inhibitors as Possible Neuroprotective Agents", Ann. N. Y. Acad. Sci., 825:366–79 (1997).

Cosi et al., "Poly(ADP–Ribose) Polymerase Inhibitors Protect Against MPTP–induced Depletions of Striatal Dopamine and Cortical Noradrenaline in C57B1/6 Mice", Brain Res., 729:264–69 (1996).

Dawson et al., "Protection of the Brain from Ischemia", Cerebrovascular Disease, 319–25 (H. Hunt Batjer ed., 1997).

Dawson et al., "Nitric Oxide Mediates Glutamate Neurotoxicity in Primary Cortical Cultures", Proc. Natl. Acad. Sci. USA, 88:6368–71 (1991).

(List continued on next page.)

Primary Examiner—Joseph K. McKane
Assistant Examiner—Taofiq A. Solola
(74) Attorney, Agent, or Firm—Nixon & Vanderhye P.C.

(57) ABSTRACT

A compound of formula I containing at least one ring nitrogen:

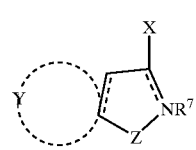

or a pharmaceutically acceptable base or acid addition salt, prodrug, metabolite, optical isomer or stereoisomer thereof.

47 Claims, 2 Drawing Sheets

OTHER PUBLICATIONS

Dawson et al., "Mechanisms of Nitric Oxide–mediated Neurotoxicity in Primary Brain Cultures", *J. Neurosci.,* 13:6, 2651–61 (1993).

Dawson et al., "Resistance to Neurotoxicity in Cortical Cultures from Neuronal Nitric Oxide Synthase–Deficient Mice", *J. Neurosci.,* 16:8, 2479–87 (1996).

Iadecola, "Bright and Dark Sides of Nitric Oxide in Ischemic Brain Injury", *Trends Neurosci.,* 20:3, 132–39 (1997).

Huang et al., "Effects of Cerebral Ischemia in Mice Deficient in Neuronal Nitric Oxide Synthase", *Science,* 265:1883–85 (1994).

Beckman et al., "Pathological Implications of Nitric Oxide, Superoxide and Peroxynitrite Formation", *Biochem. Soc. Trans.,* 21:330–34 (1993).

Cristovao et al., "Effect of a Poly(ADP–Ribose)Polymerase Inhibitor on DNA Breakage and Cytotoxicity Induced by Hydrogen Peroxide and γ–Radiation," *Terato., Carcino., and Muta.,* 16:219–27 (1996).

Salzman et al., "Role of Peroxynitrite and Poly(ADP–Ribose) Synthase Activation Experimental Colitis," *Japanese J. Pharm.,* 75, Supp. I:15 (1997) abstract.

Southan et al., "Spontaneous Rearrangement of Aminoalkylithioureas into Mercaptoalkylguanidines, a Novel Class of Nitric Oxide Synthase Inhibitors with Selectivity Towards the Inducible Isoform", *Br. J. Pharm.,* 117:619–32 (1996).

Szabó et al., "Mercaptoethylguanidine and Guanidine Inhibitors of Nitric Oxide Synthase React with Peroxynitrite and Protect Against Peroxynitrite–induced Oxidative Damage", *J. Biol. Chem.,* 272:9030–36 (1997).

Szabó et al., "Protective Effects of an Inhibitor of Poly(ADP–Ribose) Synthetase in Collagen–Induced Arthritis," *Japanese J. Pharm.,* 75, Supp. I:102 (1997) abstract.

Bauer et al., "Modification of Growth Related Enzymatic Pathways and Apparent Loss of Tumorigenicity of a ras–transformed Bovine Endothelial Cell Line by Treatment with 5–Iodo–6–amino–1,2–benzopyrone (INH$_2$BP)", *Intl. J. Oncol.,* 8:239–52 (1996).

Hughes et al., "Induction of T Helper Cell Hyporesponsiveness in an Experimental Model of Autoimmunity by Using Nonmitogenic Anti–CD3 Monolconal Antibody", *J. Immuno.,* 153:3319–25 (1994).

Heller et al., "Inactivation of the Poly(ADP–Ribose) Polymerase Gene Affects Oxygen Radical and Nitric Oxide Toxicity in Islet Cells," *J. Biol. Chem.,* 270:19, 11176–80 (May 1995).

Zingarelli et al., "Protective Effects of Nicotinamide Against Nitric Oxide–Mediated Delayed Vascular Failure in Endotoxic Shock: Potential Involvement of PolyADP Ribosyl Synthetase," *Shock,* 5:258–64 (1996).

Cuzzocrea, "Role of Peroxynitrite and Activation of Poly(ADP–Ribose) Synthetase in the Vascular Failure Induced by Zymosan–activated Plasma," *Brit. J. Pharm.,* 122:493–503 (1997).

Suto et al., "Dihydroisoquinolinones: The Design and Synthesis of a New Series of Potent Inhibitors of Poly(ADP–Ribose) Polymerase", *Anticancer Drug Des.,* 7:107–17 (1991).

Weltin et al., "Effect of 6(5H)–Phenanthridinone, an Inhibitor of Poly(ADP–ribose) Polymerase, on Cultured Tumor Cells", *Oncol. Res.,* 6:9, 399–403 (1994) abstract.

Banasik et al., "Specific Inhibitors of Poly(ADP–Ribose) Synthetase and Mono(ADP–Ribosyl)–Transferase", *J. Biol. Chem.,* 267:3, 1569–75 (1992).

Banasik et al., "Inhibitors and Activators of ADP–Ribosylation Reactions", *Molec. Cell. Biochem.,* 138:185–97 (1994).

Milam et al., "Inhibitors of Poly(Adenosine Diphosphate–Ribose) Synthesis: Effect on Other Metabolic Processes", *Science,* 223:589–91 (1984).

Rougeot et al., "Cyclization Reactions of 2–pentynyl–4–pyrimidinones", *J. Heterocycl. Chem.,* 20:5, 1407–9 (1983) abstract.

Davies et al., "Intramolecular Cycloaddition Reactions of Mono– and Dihydroxy–pyrimidines", *J. Chem. Soc.,* 11:1293–97 (1978).

Ochiai et al., "Polarization of Heterocyclic Rings with Aromatic Character. CXLVII. Reaction of 3–Methyl–5, 6, 7, 8–tetrahydroisoquinoline–2–oxide with Acetic Anhydride", *Itsuu Kenkusho Nempo,* 16:15–23 (1971) abstract.

Granger et al., *Bull. Soc. Chim., Fr.,* 233, (1962) abstract.

Di Maio et al., "Photochemistry of Some N–hydroxy Lactams", *Ric. Sci.,* 38:3, 231–33 (1968).

Di Maio et al., "The Action of Hyponitrous Acid on Ketonic Compounds. II. 1–Hydrinadanone", *Gazz. Chim. Ital.,* 91:1124–32 (1961) abstract.

Di Maio et al., "Ring Enlargement: The Schmidt Reaction on 1–hydrindanone", *Gazz. Chim. Ital.,* 91:1345–51 (1961) abstract.

Di Maio et al., "The Behavior of Some Cyclic Hydroxamic Acids at Elevated Temperatures", *Gazz. Chim. Ital.,* 94:5, 590–94 (1964) abstract.

Baer et al., "Synthesis of the Isoquinoline System from o–Phthalaldehyde and Nitromethane", *Angew. Chem.,* 76:1, 50 (1964), abstract.

White et al., "Quinoline Analogues of Ortho–Quinodimethane", *Tetrahedron Letters,* 36:33, 5983–86 (1995).

White et al., "Dihydrothiophenes as Precursors to Fused Quinolines, Quinolones and Coumarins via o–Quinodimethane Intermediates", *Tetrahedron,* 52:9, 3117–34 (1996).

Brown et al., "Reaction of Ethyl 2–Oxycyclopentane–carboxylate with Arylamines. Part I. The Preparation of 2,3–dihydro–α–quinindones (2,3,4, 5–tetrahydro–4–oxo–1H–cyclopenta [c]quinolines)", *J. Chem. Soc.,* 4295–98 (1961).

Reisch, "Chemistry of Natural Substances. VII. Furoquinoline Derivatives By Condensation of Ethyl 2–Propynyl Malonate with Aromatic Amines", *Arch Pharm. Ber. Dtsch. Pharm. Ges.,* 300:6, 533–39 (1967) abstract.

Eisch et al., "Studies on Nonpyridinoid Azaaromatic Systems. 7. Synthesis and Tautomeric Character of Cyclopenta [c]quinoline (benzo[c] [2]pyrindine)", *J. Org. Chem.,* 43:11, 2190–96 (1978).

Castan et al., "New Arylpiperazine Derivatives with High Affinity for 5–HT$_3$ Receptor Sites", *Med. Chem. Res.,* 6:2, 81–101 (1996).

Reid et al., "Reactions of Cyclic Enamines. III. Synthesis of N–Heterocycles from Cycloalkenylamine–isocyanate or—isothiocyanate Adducts", *Ann. Chem.,* 688:177–88 (1965).

Reid et al., "Reactions with Cyclic Enamines. I. Reaction of Cycloalkene–amines with Phenyl Isocyanate and Phenylisothiocyanate", *Ann.,* 673:132–36 (1964) abstract.

Johnson, "The Synthesis of N–Alkyl–2–Oxocyclopentane–Carboxyamides", *J. Chem. Soc.,* 1624–28 (1958).

Masamune et al., "Condensed Polynuclear Perhydro Compounds Containing Nitrogen. XII. Synthesis and Exhaustive Methylation of 5,6,6a,7,8,9,10,10a–Octahydro–phenanthridines and Related Compounds", *J. Org. Chem.,* 29:3, 681–85 (1964).

Naito et al., "Asymmetric Photocyclization of N–α,β–Unsaturated Acylanilides", *Heterocycles,* 22:2, 237–40 (1984).

Michailidis et al., "Hexahydrogenated Derivatives of Phenanthridone Obtained by Birch Reaction", *C. R. Acad. Sci.,* 275:17, 961–64 (1972) abstract.

Ninomiya et al., "Photocyclization of Enamides. V. Photocyclization of α,β–Unsaturated Anilides", *J. Chem. Soc.,* 1:14, 1747–51 (1974) abstract.

Taylor et al., "Phenanthridine Syntheses Via the Diels–Alder Reaction. A New Route to 6(5)–Phenan–thridinone", *J. Am. Chem. Soc.,* 78:5104–8 (1956).

Bailey et al., Reactions of p–Toluenesulfonyl Azide with Derivatives of Cyclohept– Cyclooctindole, *J. Chem. Soc.,* 1:7, 763–70 (1974).

Blount et al., "Stereoisomerism in Polycyclic Systems. Part VI.", *J. Chem. Soc.,* 1979, 1984 (1929).

OXO-SUBSTITUTED COMPOUNDS, PROCESS OF MAKING, AND COMPOSITIONS AND METHODS FOR INHIBITING PARP ACTIVITY

This application is a Division of application Ser. No. 09/079,509 filed May 15, 1998 Now abandoned Which is a Continuation in Part of Ser. No. 08/922,520 filed Sep. 3, 1997 now abandoned.

BACKGROUND OF THE INVENTION

1. Field of the Invention

The invention relates to inhibitors of the nucleic enzyme poly(adenosine 5'-diphospho-ribose)polymerase ["poly (ADP-ribose)polymerase" or "PARP", which is also sometimes called "PARS" for poly(ADP-ribose) synthetase]. More particularly, the invention also relates to the use of PARP inhibitors to prevent and/or treat neural tissue damage resulting from ischemia and reperfusion injury, neurological disorders and other neurodegenerative diseases; to prevent or treat vascular stroke; to treat or prevent cardiovascular disorders; or to treat other disorders such as arthritis, diabetes, septic shock (such as endotoxic shock); inflammatory disorders of the bowel (such as colitis and Crohn's disease); and cancer.

2. Description of the Prior Art

Poly(ADP-ribose)polymerase ("PARP") is an enzyme located in the nuclei of cells of various organs, including muscle, heart and brain cells. PARP plays a physiological role in the repair of strand breaks in DNA. Once activated by damaged DNA fragments, PARP catalyzes the attachment of up to 100 ADP-ribose units to a variety of nuclear proteins, including histones and PARP itself. While the exact range of functions of PARP has not been fully established, this enzyme is thought to play a role in enhancing DNA repair.

During major cellular stresses, however, the extensive activation of PARP can rapidly lead to cell death through depletion of energy stores. Four molecules of ATP are consumed for every molecule of NAD (the source of ADP-ribose) regenerated. Thus, NAD, the substrate of PARP, is depleted by massive PARP activation and, in the efforts to re-synthesize NAD, ATP may also be depleted.

It has been reported that PARP activation plays a key role in both NMDA- and NO-induced neurotoxicity, as shown by the use of PARP inhibitors to prevent such toxicity in cortical cultures in proportion to their potencies as inhibitors of this enzyme (Zhang et al., "Nitric Oxide Activation of Poly(ADP-Ribose) Synthetase in Neurotoxicity", *Science*, 263:687–89 (1994)); and in hippocampal slices (Wallis et al., "Neuroprotection Against Nitric Oxide Injury with Inhibitors of ADP-Riboslation", *NeuroReport*, 5:3, 245–48 (1993)). The potential role of PARP inhibitors in treating neurodegenerative diseases and head trauma has thus been known. Research, however, continues to pinpoint the exact mechanisms of their salutary effect in cerebral ischemia (Endres et al., "Ischemic Brain Injury is Mediated by the Activation of Poly(ADP-Ribose)-Polymerase", *J. Cereb. Blood Flow Metabol.*, 17:1143–51 (1997)) and in traumatic brain injury (Wallis et al., "Traumatic Neuroprotection with Inhibitors of Nitric Oxide and ADP-Ribosylation, *Brain Res.*, 710:169–77 (1996)).

It has been demonstrated that single injections of PARP inhibitors have reduced the infarct size caused by ischemia and reperfusion of the heart or skeletal muscle in rabbits. In these studies, a single injection of the PARP inhibitor, 3-aminobenzamide (10 mg/kg), either one minute before occlusion or one minute before reperfusion, caused similar reductions in infarct size in the heart (32–42%). Another PARP inhibitor, 1,5-dihydroxy-isoquinoline (1 mg/kg), reduced infarct size by a comparable degree (38–48%). Thiemermann et al., "Inhibition of the Activity of Poly(ADP Ribose) Synthetase Reduces Ischemia-Reperfusion Injury in the Heart and Skeletal Muscle", *Proc. Natl. Acad. Sci. USA*, 94:679–83 (1997). This finding has suggested that PARP inhibitors might be able to salvage previously ischemic heart or skeletal muscle tissue.

PARP activation has also been shown to provide an index of damage following neurotoxic insults by glutamate (via NMDA receptor stimulation), reactive oxygen intermediates, amyloid β-protein, n-methyl-4-phenyl-1,2,3, 6-tetrahydropyridine (MPTP) and its active metabolite N-methyl-4-phenylpyridine (MPP$^+$), which participate in pathological conditions such as stroke, Alzheimer's disease and Parkinson's disease. Zhang et al., "Poly(ADP-Ribose) Synthetase Activation: An Early Indicator of Neurotoxic DNA Damage", *J. Neurochem.*, 65:3, 1411–14 (1995). Other studies have continued to explore the role of PARP activation in cerebellar granule cells in vitro and in MPTP neurotoxicity. Cosi et al., "Poly(ADP-Ribose) Polymerase (PARP) Revisited. A New Role for an Old Enzyme: PARP Involvement in Neurodegeneration and PARP Inhibitors as Possible Neuroprotective Agents", *Ann. N. Y. Acad. Sci.*, 825:366–79 (1997); and Cosi et al., "Poly(ADP-Ribose) Polymerase Inhibitors Protect Against MPTP-induced Depletions of Striatal Dopamine and Cortical Noradrenaline in C57B1/6 Mice", *Brain Res.*, 729:264–69 (1996).

Neural damage following stroke and other neurodegenerative processes is thought to result from a massive release of the excitatory neurotransmitter glutamate, which acts upon the N-methyl-D-aspartate (NMDA) receptors and other subtype receptors. Evidence includes findings in many animal species, as well as in cerebral cortical cultures treated with glutamate or NMDA, that glutamate receptor antagonists block neural damage following vascular stroke. Dawson et al., "Protection of the Brain from Ischemia", *Cerebrovascular Disease*, 319–25 (H. Hunt Batjer ed., 1997).

The stimulation of NMDA receptors, in turn, activates the enzyme neuronal nitric oxide synthase (NNOS), which causes the formation of nitric oxide (N,O), which more directly mediates neurotoxicity. Protection against NMDA neurotoxicity has occurred following treatment with NOS inhibitors. See Dawson et al., "Nitric Oxide Mediates Glutamate Neurotoxicity in Primary Cortical Cultures", *Proc. Natl. Acad. Sci. USA*, 88:6368–71 (1991); and Dawson et al., "Mechanisms of Nitric Oxide-mediated Neurotoxicity in Primary Brain Cultures", *J. Neurosci.*, 13:6, 2651–61 (1993). Protection against NMDA neurotoxicity can also occur in cortical cultures from mice with targeted disruption of NNOS. See Dawson et al., "Resistance to Neurotoxicity in Cortical Cultures from Neuronal Nitric Oxide Synthase-Deficient Mice", *J. Neurosci.*, 16:8, 2479–87 (1996).

It is known that neural damage following vascular stroke is markedly diminished in animals treated with NOS inhibitors or in mice with NNOS gene disruption. Iadecola, "Bright and Dark Sides of Nitric Oxide in Ischemic Brain Injury", *Trends Neurosci.*, 20:3, 132–39 (1997); and Huang et al., "Effects of Cerebral Ischemia in Mice Deficient in Neuronal Nitric Oxide Synthase", *Science*, 265:1883–85 (1994). See also, Beckman et al., "Pathological Implications of Nitric Oxide, Superoxide and Peroxynitrite Formation", *Biochem. Soc. Trans.*, 21:330–34 (1993). Either NO or peroxynitrite can cause DNA damage, which activates PARP. Further support for this is provided in Szaboet al., "DNA Strand Breakage, Activation of Poly(ADP-Ribose) Synthetase, and Cellular Energy Depletion are Involved in the Cytotoxicity in Macrophages and Smooth Muscle Cells Exposed to Peroxynitrite", *Proc. Natl. Acad. Sci. USA*, 93:1753–58 (1996).

Zhang et al., U.S. Pat. No. 5,587,384 issued Dec. 24, 1996, discusses the use of certain PARP inhibitors, such as benzamide and 1,5-dihydroxy-isoquinoline, to prevent NMDA-mediated neurotoxicity and, thus, treat stroke, Alzheimer's disease, Parkinson's disease and Huntington's disease. However, it has now been discovered that Zhang et al. may have been in error in classifying in vivo neurotoxicity as NMDA-mediated neurotoxicity. Rather, it may have been more appropriate to classify the neurotoxicity as glutamate neurotoxicity. See Zhang et al., "Nitric Oxide Activation of Poly(ADP-Ribose) Synthetase in Neurotoxicity", *Science*, 263:687–89 (1994). See also, Cosi et al., Poly(ADP-Ribose)-Polymerase Inhibitors Protect Against MPTP-induced Depletions of Striatal Dopamine and Cortical Noradrenaline in C57B1/6 Mice", *Brain Res.*, 729:264–69 (1996).

It is also known that PARP inhibitors effect DNA repair generally. Cristovao et al., "Effect of a Poly(ADP-Ribose) Polymerase Inhibitor on DNA Breakage and Cytotoxicity Induced by Hydrogen Peroxide and γ-Radiation," *Terato., Carcino., Muta.*, 16:219–27 (1996), discusses the effect of hydrogen peroxide and γ-radiation on DNA strand breaks in the presence of and in the absence of 3-aminobenzamide, a potent inhibitor of PARP. Cristovao et al. observed a PARP-dependent recovery of DNA strand breaks in leukocytes treated with hydrogen peroxide.

Evidence also exists that PARP inhibitors are useful for treating inflammatory bowel disorders. Salzman et al., "Role of Peroxynitrite and Poly(ADP-Ribose)Synthase Activation Experimental Colitis," *Japanese J. Pharm.*, 75, Supp. I:15 (1997), discusses the ability of PARP inhibitors to prevent or treat colitis. Colitis was induced in rats by intraluminal administration of the hapten trinitrobenzene sulfonic acid in 50% ethanol. Treated rats received 3-aminobenzamide, a specific inhibitor of PARP activity. Inhibition of PARP activity reduced the inflammatory response and restored the morphology and the energetic status of the distal colon. See also, Southan et al., "Spontaneous Rearrangement of Aminoalkylthioureas into Mercaptoalkylguanidines, a Novel Class of Nitric Oxide Synthase Inhibitors with Selectivity Towards the Inducible Isoform", *Br. J. Pharm.*, 117:619–32 (1996); and Szabó et al., "Mercaptoethylguanidine and Guanidine Inhibitors of Nitric Oxide Synthase React with Peroxynitrite and Protect Against Peroxynitrite-induced Oxidative Damage", *J. Biol. Chem.*, 272:9030–36 (1997).

Evidence also exists that PARP inhibitors are useful for treating arthritis. Szabó et al., "Protective Effects of an Inhibitor of Poly(ADP-Ribose)Synthetase in Collagen-Induced Arthritis," *Japanese J. Pharm.*, 75, Supp. I:102 (1997), discusses the ability of PARP inhibitors to prevent or treat collagen-induced arthritis. See also, Szabó et al., "DNA Strand Breakage, Activation of Poly(ADP-Ribose) Synthetase, and Cellular Energy Depletion are Involved in the Cytotoxicity in Macrophages and Smooth Muscle Cells Exposed to Peroxynitrite," *Proc. Natl. Acad. Sci. USA*, 93:1753–58 (March 1996); Bauer et al., "Modification of Growth Related Enzymatic Pathways and Apparent Loss of Tumorigenicity of a ras-transformed Bovine Endothelial Cell Line by Treatment with 5-Iodo-6-amino-1,2-benzopyrone ($INH_2BP$)", *Intl. J. Oncol.*, 8:239–52 (1996); and Hughes et al., "Induction of T Helper Cell Hyporesponsiveness in an Experimental Model of Autoimmunity by Using Nonmitogenic Anti-CD3 Monoclonal Antibody", *J. Immuno.*, 153:3319–25 (1994).

Further, PARP inhibitors appear to be useful for treating diabetes. Heller et al., "Inactivation of the Poly(ADP-Ribose)Polymerase Gene Affects Oxygen Radical and Nitric Oxide Toxicity in Islet Cells," *J. Biol. Chem.*, 270:19, 11176–80 (May 1995), discusses the tendency of PARP to deplete cellular NAD+ and induce the death of insulin-producing islet cells. Heller et al. used cells from mice with inactivated PARP genes and found that these mutant cells did not show NAD+ depletion after exposure to DNA-damaging radicals. The mutant cells were also found to be more resistant to the toxicity of NO.

Further still, PARP inhibitors have been shown to be useful for treating endotoxic shock or septic shock. Zingarelli et al., "Protective Effects of Nicotinamide Against Nitric Oxide-Mediated Delayed Vascular Failure in Endotoxic Shock: Potential Involvement of PolyADP Ribosyl Synthetase," *Shock*, 5:258–64 (1996), suggests that inhibition of the DNA repair cycle triggered by poly(ADP ribose) synthetase has protective effects against vascular failure in endotoxic shock. Zingarelli et al. found that nicotinamide protects against delayed, NO-mediated vascular failure in endotoxic shock. Zingarelli et al. also found that the actions of nicotinamide may be related to inhibition of the NO-mediated activation of the energy-consuming DNA repair cycle, triggered by poly(ADP ribose) synthetase. See also, Cuzzocrea, "Role of Peroxynitrite and Activation of Poly(ADP-Ribose) Synthetase in the Vascular Failure Induced by Zymosan-activated Plasma," *Br. J. Pharm.*, 122:493–503 (1997).

Yet another known use for PARP inhibitors is treating cancer. Suto et al., "Dihydroisoquinolinones: The Design and Synthesis of a New Series of Potent Inhibitors of Poly(ADP-Ribose) Polymerase", *Anticancer Drug Des.*, 7:107–17 (1991), discloses processes for synthesizing a number of different PARP inhibitors. In addition, Suto et al., U.S. Pat. No. 5,177,075, discusses several isoquinolines used for enhancing the lethal effects of ionizing radiation or chemotherapeutic agents on tumor cells. Weltin et al., "Effect of 6(5H)-Phenanthridinone, an Inhibitor of Poly (ADP-ribose) Polymerase, on Cultured Tumor Cells", *Oncol. Res.*, 6:9, 399–403 (1994), discusses the inhibition of PARP activity, reduced proliferation of tumor cells, and a marked synergistic effect when tumor cells are co-treated with this compound and an alkylating drug.

Large numbers of known PARP inhibitors have been described in Banasik et al., "Specific Inhibitors of Poly (ADP-Ribose) Synthetase and Mono(ADP-Ribosyl)-Transferase", *J. Biol. Chem.*, 267:3, 1569–75 (1992), and in Banasik et al., "Inhibitors and Activators of ADP-Ribosylation Reactions", *Molec. Cell. Biochem.*, 138:185–97 (1994). The former reference discloses 6(5H)-phenanthridinone and 2-nitro-6(5H)-phenanthridinone.

However, the approach of using these PARP inhibitors to reduce NMDA-receptor stimulation, or to treat or prevent neural tissue damage caused by NO, ischemia and reperfusion of the heart, arthritis, diabetes, endotoxic or septic shock, inflammatory diseases of the bowel (such as colitis and Crohn's disease), and cancer, has been limited in effect. For example, side effects have been observed with some of the best-known PARP inhibitors, as discussed in Milam et al., "Inhibitors of Poly(Adenosine Diphosphate-Ribose)

Synthesis: Effect on Other Metabolic Processes", *Science*, 223:589–91 (1984). Specifically, the PARP inhibitors 3-aminobenzamide and benzamide not only inhibited the action of PARP but also were shown to affect cell viability, glucose metabolism, and DNA synthesis. Thus, it was concluded that the usefulness of these PARP inhibitors may be severely restricted by the difficulty of finding a dose small enough to inhibit the enzyme without producing additional metabolic effects.

Accordingly, there remains a need for a composition containing PARP inhibitors that produce more potent and reliable effects, particularly with respect to vascular stroke, with fewer side effects.

Multicyclic oxo-substituted compounds other than the compounds of the invention are known. These include, but are not limited to:

I. 3-(5-Hexynyl)-2,4a,5,6,7,7a-hexahydro-1H-cyclopenta[c]-pyridin-1-one, shown in Rougeot et al., "Cyclization Reactions of 2-pentynyl-4-pyrimidinones", *J. Heterocycl. Chem.*, 20:5, 1407–9 (1983);

II. 2,4a,5,6,7,7a-Hexahydro-3-methyl-1H-cyclopenta-[c]pyridin-1-one, shown in Davies et al., "Intramolecular Cycloaddition Reactions of Mono- and Dihydroxy-pyrimidines", *J. Chem. Soc.*, 11:1293–97 (1978);

III. 2,4a,5,6,7,7a-Hexahydro-3-phenyl--1H-cyclopenta-[c]pyridin-1-one, shown in Davies et al., "Intramolecular Cycloaddition Reactions of Mono- and Dihydroxy-pyrimidines", *J. Chem. Soc.*, 11:1293–97 (1978);

IV. Octahydro-3-methyl-1(2H)-isoquinolinone, shown in Ochiai et al., "Polarization of Heterocyclic Rings with Aromatic Character. CXLVII. Reaction of 3-Methyl-5,6,7,8-tetrahydroisoquinoline-2-oxide with Acetic Anhydride", *Itsuu Kenkusho Nempo*, 16:15–23 (1971);

V. Octahydro-<2>pyrindin-1-one, shown in Granger et al., *Bull. Soc. Chim. Fr.*, 233, (1962);

VI. Octahydro-isocarbostyril, shown in:
  (a) Di Maio et al., "Photochemistry of Some N-hydroxy Lactams", *Ric. Sci.*, 38:3, 231–33 (1968);
  (b) Di Maio et al., "The Action of Hyponitrous Acid on Ketonic Compounds. II. 1-Hydrinadanone", *Gazz. Chim. Ital.*, 91:1124–32 (1961);
  (c) Di Maio et al., "Ring Enlargement: The Schmidt Reaction on 1-hydrindanone", *Gazz. Chim. Ital.*, 91:1345–51 (1961)
  (d) Di Maio et al., "The Behavior of Some Cyclic Hydroxamic Acids at Elevated Temperatures", *Gazz. Chim. Ital.*, 94:5, 590–94 (1964);
  (e) Baer et al., "Cyclizations of Dialdehydes with Nitromethane. XII. Phthalaldehyde", *J. Org. Chem.*, 29:11, 3180–85 (1964);
  (f) Ochiai et al., "Polarization of Aromatic Heterocyclic Compounds. CXX. A New Synthesis of 1-Halo-5,6,7,8-tetrahydroisoquinoline", *Pharm. Bull.*, 5:289–91 (1957); and
  (g) Baer et al., "Synthesis of the Isoquinoline System from o-Phthalaldehyde and Nitromethane", *Angew. Chem.*, 76:1, 50 (1964);

VII. 3,5-Dihydro--1H-thieno<3,4-c>quinolin-4-one shown in:
  (a) White et al., "Quinoline Analogues of Ortho-Quinodimethane", *Tetrahedron Letters*, 36:33, 5983–86 (1995); and
  (b) White et al., "Dihydrothiophenes as Precursors to Fused Quinolines, Quinolones and Coumarins via o-Quinodimethane Intermediates", *Tetrahedron*, 52:9, 3117–34 (1996);

VIII. 7(or 9)-Chloro-1,2,3,5-tetrahydro-4H-cyclopenta-[c] quinoline-4-one, 1,2,3,4-tetrahydro-7(or 9)-methyl-4H-cyclopenta[c]quinoline-4-one and 1,2,3,5-tetrahydro-4H-cyclopenta[c]quinolin-4-one, shown in:
  (a) Brown et al., "Reaction of Ethyl 2-Oxocyclopentane-carboxylate with Arylamines. Part I. The Preparation of 2,3-dihydro-α-quinindones (2,3,4,5-tetrahydro-4-oxo-1H-cyclopenta[c]quinolines)", *J. Chem. Soc.*, 4295–98 (1961);
  (b) 1,2,3,5-Tetrahydro-4H-cyclopenta-[c]quinoline-4-one, Reisch, "Chemistry of Natural Substances. VII. Furoquinoline Derivatives By Condensation of Ethyl 2-Propynyl Malonate with Aromatic Amines", *Arch. Pharm. Ber. Dtsch. Pharm. Ges.*, 300:6, 533–39 (1967);
  (c) 1,2,3,5-Tetrahydro-4H-cyclopenta-[c]quinoline-4-one, Eisch et al., "Studies on Nonpyridinoid Azaaromatic Systems. 7. Synthesis and Tautomeric Character of Cyclopenta[c]quinoline (benzo [c] [2]pyrindine)", *J. Org. Chem.*, 43:11, 2190–96 (1978);
  (d) 1,2,3,5-Tetrahydro-4H-cyclopenta-[c]quinoline-4-one, Castan et al., "New Arylpiperazine Derivatives with High Affinity for 5-$HT_3$ Receptor Sites", *Med. Chem. Res.*, 6:2, 81–101 (1996);
  (e) 1,2,3,5-Tetrahydro-4H-cyclopenta-[c]quinoline-4-one, Reid et al., "Reactions of Cyclic Enamines. III. Synthesis of N-Heterocycles from Cycloalkenylamine-isocyanate or -isothiocyanate Adducts", *Ann. Chem.*, 688:177–88 (1965); and
  (f) 1,2,3,5-Tetrahydro-4H-cyclopenta[c]quinoline-4-one, Reid et al., "Reactions with Cyclic Enamines. I. Reaction of Cycloalkene-amines with Phenyl Isocyanate and Phenylisothiocyanate", *Ann.*, 673:132–36 (1964);

IX. 2-Hydroxy-3,4-cyclopentenoquinoline, shown in Johnson, "The Synthesis of N-Alkyl-2-Oxocyclopentane-Carboxyamides", *J. Chem. Soc.*, 1624–28 (1958);

X. 1,2,4,6-Tetrahydro-5H-thiopyrano[3,4-c]quinoline-5-one, shown in Castan et al., "New Arylpiperazine Derivatives with High Affinity for 5-$HT_3$ Receptor Sites", *Med. Chem. Soc.*, 6:2, 81–101 (1996);

XI. 6a,7,8,9,10,10a-Hexahydro-trans-6(5H)-phenanthridinone, shown in:
  (a) Masamune et al., "Condensed Polynuclear Perhydro Compounds Containing Nitrogen. XII. Synthesis and Exhaustive Methylation of 5,6,6a,7,8,9,10,10a-Octahydro-phenanthridines and Related Compounds", *J. Org. Chem.*, 29:3, 681–85 (1964);
  (b) 6a,7,8,9,10,10a-Hexahydro-cis(±)6(5H)-phenanthridinone, Naito et al., "Asymmetric Photocyclization of N-α, β-Unsaturated Acylanilides", *Heterocycles*, 22:2, 237–40 (1934), along with the (6aR-trans)- and (6aS-trans)-stereoisomers of the same compound;
  (c) Michailidis et al., "Hexahydrogenated Derivatives of Phenanthridone Obtained by Birch Reaction", *C. R. Acad. Sci.*, 275:17, 961–64 (1972), with cis and trans stereoisomers of the same compound;
  (d) Ninomiya et al., "Photocyclization of Enamides. V. Photocyclization of α, β-Unsaturated Anilides", *J. Chem. Soc.*, 1:14, 1747–51 (1974), with cis stereoisomer; and
  (e) Taylor et al., "Phenanthridine Syntheses Via the Diels-Alder Reaction. A New Route to 6(5)-Phenanthridinone", *J. Am. Chem. Soc.*, 78:5104–8 (1956);

XII. 7,8,9,10-tetrahydro-6(5H), as shown in
  (a) Masamune et al., "The Synthesis and Exhaustive Methylation of 5,6,7,8,9,10,6a,10a-Octahydrophenanthridines and Related Compounds, *J. Org. Chem.*, 29:3, 681–85 (1964);
  (b) Bailey et al., "Reactions of p-Toluenesulfonyl Azide with Derivatives of Cyclohept- and Cyclooctindole, *J. Chem. Soc.*, 1:7, 763–70 (1974);
  (c) Reid et al., "Reactions of Cyclic Enamines. III. Synthesis of N-Heterocycles from Cycloalkenylamine-isocyanate or -isothiocyanate Adducts", *Ann. Chem.*, 688:177–88 (1965); and
  (d) Reid et al., "Reactions with Cyclic Enamines. I. Reaction of Cycloalkene-amines with Phenyl Isocyanate and Phenylisothiocyanate", *Ann.*, 132–36 (1964); and
XIII. 1,2,3,3a,5,9b-Hexahydro-cyclopenta<c>quinolin-4-one, shown in Blount et al., "Stereoisomerism in Polycyclic Systems. Part VI.", *J. Chem. Soc.*, 1979, 1984 (1929).

1,2,3,5,-Tetrahydrocyclopenta[c]quinolin-4-one, as cited in Castan et al., "New Arylpiperazine Derivatives with High Affinity for 5-$HT_3$ Receptor Sites", *Med. Chem. Res.*, 6:2, 81–101 (1996), is an intermediate in the preparation of new arylpiperazine derivatives with high affinity for serotoninergic $S_3$ receptor sites in relation to structure. However, it is not believed that this intermediate or any of the previously cited oxo-substituted compounds have been shown to inhibit PARP activity.

Other oxo-substituted compounds are disclosed in:
  (1) Taylor et al., "Phenanthridine Syntheses Via the Diels-Alder Reaction. A New Route to 6(5)-Phenanthridinone", *J. Am. Chem. Soc.*, 78:5104–8 (1956);
  (2) Reid et al., "Reactions of Cyclic Enamines. III. Synthesis of N-Heterocycles from Cycloalkenylamine-isocyanate or -isothiocyanate Adducts", *Ann. Chem.*, 688:177–88 (1965);
  (3) Gauthier, U.S. Pat. No. 3,838,134, disclosing phenanthridinones used as antiviral agents; and
  (4) Winter et al., U.S. Pat. No. 4,382,943, disclosing anti-allergic aryl ether derivatives. It is not believed that any of these oxo-substituted compounds have been shown to inhibit PARP activity.

Other structurally distinguishable compounds have been disclosed for medical treatments and other uses. For example, Winter et al., U.S. Pat. No. 4,382,943, discloses the use of dibenzo-[b] [d]pyran-6-one as an antihistamine, an anti-oedematous agent and an antiphlogistic agent. Meyer et al., U.S. Pat. No. 4,169,897, entitled "2,7-Bis-Basic Ethers of 9-Phenanthrol and 9-Loweralkoxy Phenanthrol", discloses certain phenanthrenes and phenanthrinidinones useful for preventing or inhibiting viral infections.

Hunger et al, U.S. Pat. No. 4,082,741, entitled "Disazo Pigments Derived from 3,8-Diamino-Phenanthridone-(10)", discloses compounds useful for pigments suitable for preparing of printing inks, color lacquers and dispersion paints, which are used to dye rubber, plastic materials, and natural or synthetic resins. Montgomery, U.S. Pat. No. 3,291,801, discloses octahydro-6(5)-phenanthridinones that may be converted to the corresponding 6(5)-phenanthridinones, which are useful as intermediates for forming therapeutically active compounds. Hegar, U.S. Pat. No. 3,507,872, entitled "Indolyl-Quinolinium Dyestuffs", discloses water soluble basic dyestuffs comprising α-pyridones or γ-pyridones.

Schohe et al., U.S. Pat. No. 5,274,097 discloses a number of 1,3-di-substituted pyrrolidines, which can be substituted with, among many others, the following radical:

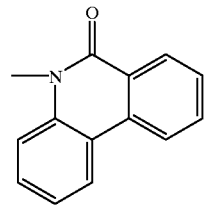

These structures are said to have high affinity for cerebral 5-hydroxytryptamine receptors of the 5-$HT_1$ type, which are said to combat diseases distinguished by disturbances of the serotoninergic system, in particular, those involved with receptors having a high affinity for 5-hydroxytryptamine (5-$HT_1$) type.

The inventors have now discovered that selected oxo-substituted PARP inhibitors can ameliorate neural tissue damage, including that following focal ischemia and reperfusion injury. Generally, inhibition of PARP activity spares perhaps as yet undiscovered, in addition to the production of free radicals and NO.

SUMMARY OF THE INVENTION

The present invention contemplates a compound of formula I containing at least one ring nitrogen:

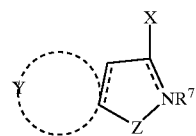

I or a pharmaceutically acceptable base or acid addition salt, prodrug, metabolite, optical isomer or stereoisomer thereof, wherein:
  X is double-bonded oxygen or —OH;
  when $R^7$ is present, it is hydrogen or lower alkyl;
  Y represents the atoms necessary to form a fused mono-, bi -or tricyclic, carbocyclic or heterocyclic ring, wherein each individual ring has 5–6 ring member atoms; and
  Z is (i) —$CHR^2CHR^3$— wherein $R^2$ is in the meta-position and $R^3$ is in the ortho-position relative to said ring nitrogen of formula I, and $R^2$ and $R^3$ are independently hydrogen, alkyl, aryl, or aralkyl;
    (ii) —$R^6C$=$CR^3$— wherein $R^6$ is meta to the ring nitrogen, and $R^3$ and $R^6$ are independently hydrogen, lower alkyl, aryl, aralkyl, halo, —$NO_2$, —$COOR^7$, or —$NR^7R^8$ where $R^3$ is independently hydrogen or $C_1$–$C_9$ alkyl, or $R^6$ and $R^3$, taken together, form a fused aromatic ring, wherein each individual ring has 5–6 ring members;
    (iii) —$R^2C$=N—;
    (iv) —$CR^2(OH)$—$NR^7$—; or
    (v) —C(O)—$NR^7$—,
  with the provisos that:
    (a) when X is double-bonded oxygen and Z is —$CHR^2CHR^3$—, $R^3$ cannot be hydrogen or methyl;
    (b) when X is double-bonded oxygen and Z is —$R^6C$=$CR^3$—, $R^3$ cannot be methyl, phenyl, or —$(CH_2)_4$—C≡CH;

(c) when $R^3$ and $R^6$ are taken together to form a fused aromatic ring, Y cannot be a ring selected from the group consisting of:

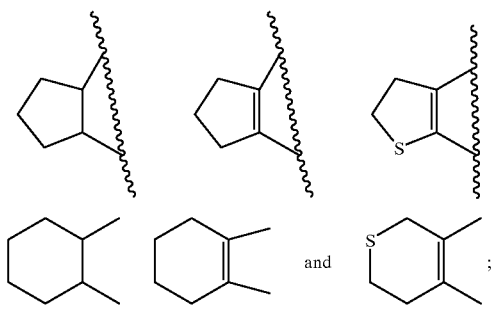

and (d) when X, Y and Z, taken together, form a phenanthridone, a phenanthridinone, a phenanthrene, or a phenanthridine nucleus with an amino group or an aminoalkoxylene group in the 3-position, the 8-position cannot also be substituted with an amino group or an aminoalkoxylene group; and (e) when X, Y and Z, taken together, form a phenanthridinone ring system, the 2-position cannot be either unsubstituted or substituted with a nitro group.

In another embodiment, a process for making the compound of formula I comprises the step of contacting an intermediate of formula IV:

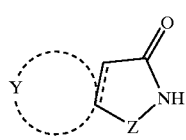

IV wherein Y and Z are as defined above, with a nitrogen-insertion agent to form a compound of formula V:

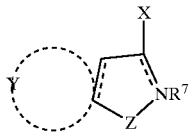

V

In yet another embodiment, the pharmaceutical composition of the invention comprises a pharmaceutically acceptable carrier and a compound of formula I containing at least one ring nitrogen:

I or a pharmaceutically acceptable base or acid addition salt, prodrug, metabolite, optical isomer or stereoisomer thereof, wherein:

X is double-bonded oxygen or —OH;

when $R^7$ is present, it is hydrogen or lower alkyl;

Y represents the atoms necessary to form a fused mono-, bi- or tricyclic, carbocyclic or heterocyclic ring, wherein each individual ring has 5–6 ring member atoms; and Z is (i) —CHR²CHR³— wherein $R^2$ is in the meta-position and $R^3$ is in the ortho-position relative to said ring nitrogen of formula I, and $R^2$ and $R^3$ are independently hydrogen, alkyl, aryl, or aralkyl;

(ii) —R⁶C═CR³— wherein $R^6$ is meta to the ring nitrogen, and $R^3$ and $R^6$ are independently hydrogen, lower alkyl, aryl, aralkyl, halo, —NO₂, —COOR⁷, or —NR⁷R⁸ where $R^8$ is independently hydrogen or $C_1$–$C_9$ alkyl, or $R^6$ and $R^3$, taken together, form a fused aromatic ring, wherein each individual ring has 5–6 ring members;

(iii) —R²C═N—;

(iv) —CR²(OH)—NR⁷—; or (v) —C(O)—NR⁷—, with the provisos that:

(a) when X is double-bonded oxygen and Z is —CHR²CHR³—, $R^3$ cannot be hydrogen or methyl;

(b) when X is double-bonded oxygen and Z is —R⁶C═CR³—, $R^3$ cannot be methyl, phenyl, or —(CH₂)₄—C≡CH;

(c) when $R^3$ and $R^6$ are taken together to form a fused aromatic ring, Y cannot be a ring selected from the group consisting of:

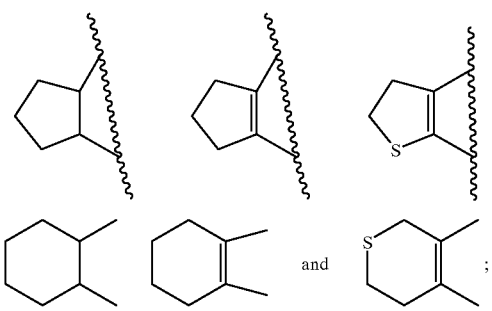

and (d) when X, Y and Z, taken together, form a phenanthridone, a phenanthridinone, a phenanthrene, or a phenanthridine nucleus with an amino group or an aminoalkoxylene group in the 3-position, the 8-position cannot also be substituted with an amino group or an aminoalkoxylene group; and (e) when X, Y and Z, taken together, form a phenanthridinone ring system, the 2-position cannot be either unsubstituted or substituted with a nitro group.

In a still further embodiment of the invention, the pharmaceutical composition of the invention comprises a pharmaceutically acceptable carrier and a compound of formula I containing at least one ring nitrogen:

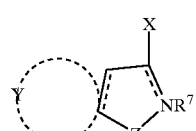

I or a pharmaceutically acceptable base or acid addition salt, prodrug, metabolite, optical isomer or stereoisomer thereof, wherein:

X is double-bonded oxygen or —OH;

when $R^7$ is present, it is hydrogen or lower alkyl;

Y represents the atoms necessary to form a fused mono-, bi- or tricyclic, carbocyclic or heterocyclic ring, wherein each individual ring has 5–6 ring member atoms; and Z is (i) —CHR²CHR³— wherein $R^2$ is in the meta-position and $R^3$ is in the ortho-position relative to said ring nitrogen of formula I, and $R^2$ and $R^3$ are independently hydrogen, alkyl, aryl, or aralkyl;

(ii) —R⁶C═CR³— wherein $R^6$ is meta to the ring nitrogen, and $R^3$ and $R^6$ are independently hydrogen, lower alkyl, aryl, aralkyl, halo, —NO₂, —COOR⁷, or —NR⁷R⁸ where $R^8$ is independently hydrogen or $C_1$–$C_9$ alkyl, or $R^6$ and $R^3$, taken together, form a fused aromatic ring, wherein each individual ring has 5–6 ring members;

(iii) —R²C═N—;

(iv) —CR²(OH)—NR⁷—; or (v) —C(O)—NR⁷—, wherein the compound of formula I is present in an amount that is sufficient to inhibit PARP activity, to effect neuronal activity not mediated by NMDA toxicity, to treat arthritis, to treat diabetes, to treat an inflammatory bowel disorder, to treat a cardiovascular disorder, to treat septic shock or to treat cancer, with the provisos that:

(a) when X is double-bonded oxygen and Z is —CHR²CHR³—, $R^3$ cannot be hydrogen or methyl;

(b) when X is double-bonded oxygen and Z is —R⁶C═CR³—, $R^3$ cannot be methyl, phenyl, or —(CH₂)₄—C≡CH;

(c) when $R^3$ and $R^6$ are taken together to form a fused aromatic ring, Y cannot be a ring selected from the group consisting of:

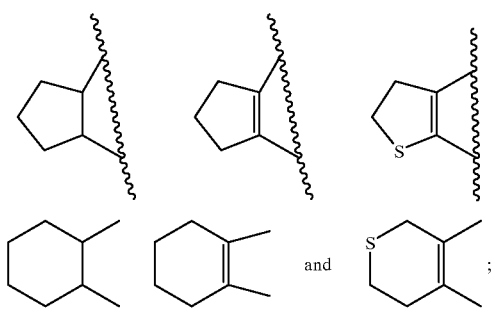

(d) when X, Y and Z, taken together, form a phenanthridone, a phenanthridinone, a phenanthrene, or a phenanthridine nucleus with an amino group or an aminoalkoxylene group in the 3-position, the 8-position cannot also be substituted with an amino group or an aminoalkoxylene group; and (e) when X, Y and Z, taken together, form a phenanthridinone ring system, the 2-position cannot be either unsubstituted or substituted with a nitro group.

In an additional embodiment, a method of inhibiting PARP activity comprises administering a compound of formula I, as described above for the pharmaceutical compositions for inhibiting PARP activity. In additional preferred embodiments, the amount of the compound administered in the methods of the invention is sufficient for effecting neuronal activity not mediated by NMDA toxicity or for treating arthritis, diabetes, and an inflammatory bowel disorder, a cardiovascular disorder, septic shock, or cancer.

DETAILED DESCRIPTION OF THE INVENTION

Oxo-substituted Compounds

Figure 1:
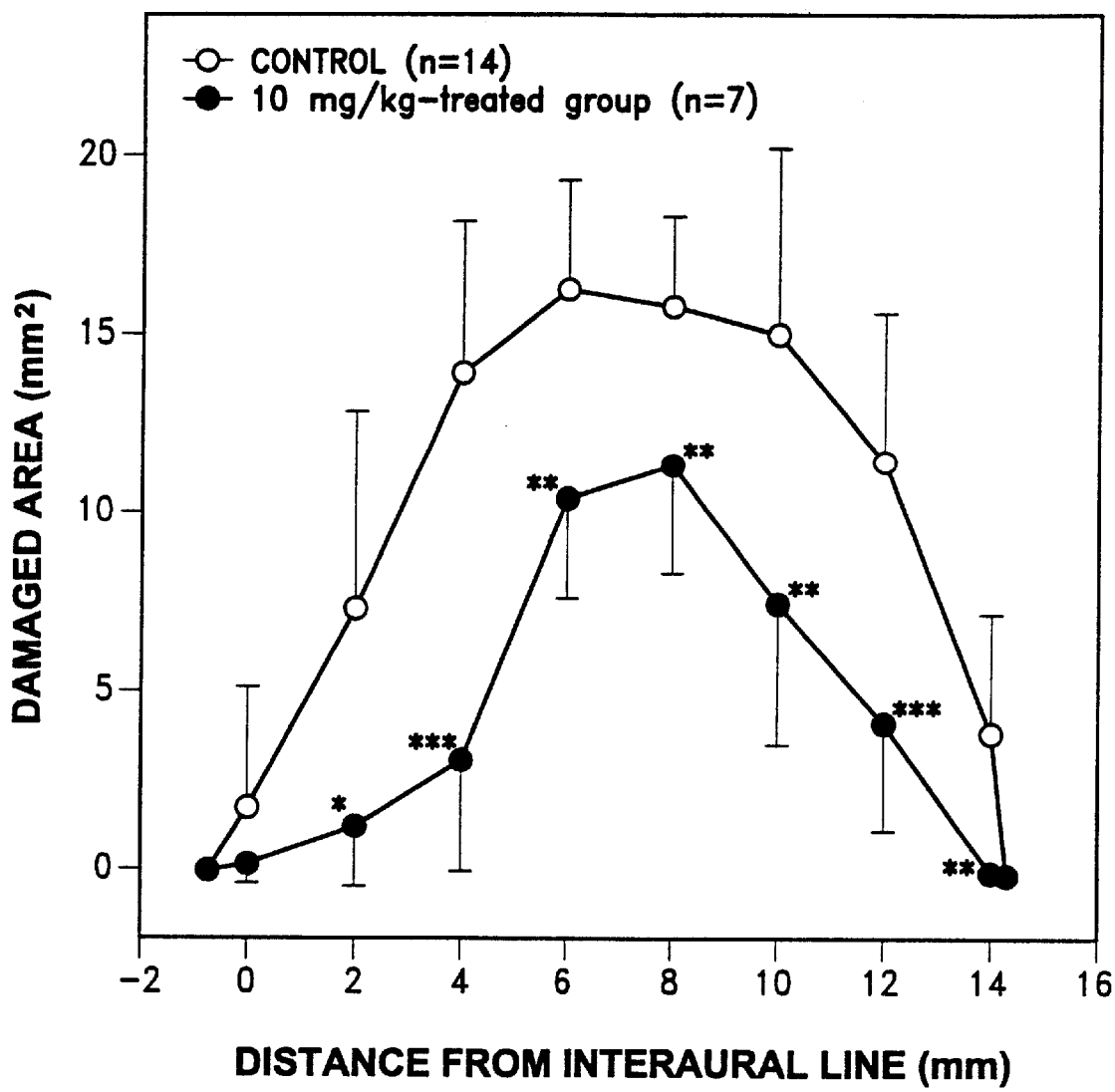
FIG. 1 shows the distribution of the cross-sectional infarct area at representative levels along the rostrocaudal axis, as measured from the interaural line in non-treated animals and in animals treated with 10 mg/kg of 3,4-dihydro-5-[4-(1-piperidinyl)-butoxy]-1(2H)-isoquinolinone.

The oxo-substituted compounds of the present invention often act as PARP inhibitors to treat or prevent neural tissue damage resulting from cerebral ischemia and reperfusion injury or neurodegenerative diseases in a mammal. In addition, these compounds can also treat or prevent cardiovascular tissue damage which can occur from cardiac ischemia or reperfusion injury. Reperfusion injury is likely to occur at the termination of cardiac bypass procedures, or following successful resuscitation of cardiac arrest, when the heart begins to re-perfuse. Further, the oxo-substituted compounds of the invention can treat or prevent other tissue damage that can occur related to PARP activation. These compounds are thought to interfere with more than the glutamate neurotoxicity and NO-mediated biological pathways. Preferably, the oxo-substituted compounds of the invention exhibit an $IC_{50}$ for inhibiting PARP in vitro of about 100 μM or lower, more preferably, about 25 μM or lower. Preferably, the oxo-substituted compounds of the invention effect a neuronal activity not mediated by NMDA.

The compound of the present invention has the formula:

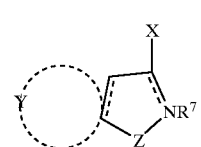

I wherein X is double-bonded oxygen or —OH. In a particularly preferred embodiment, X is double-bonded oxygen.

When $R^7$ is present, it is hydrogen or lower alkyl. Examples of useful lower alkyl groups for $R^7$ include, without limitation, methyl, ethyl, isopropyl, tert-butyl, n-pentyl, and n-hexyl. Preferably, however, $R^7$ is hydrogen.

Y in formula I represents the atoms necessary to form a fused 5- or 6-membered, or aromatic or non-aromatic carbocyclic or heterocyclic ring. Carbocyclic moieties include alicyclic and aromatic structures. When Y forms a fused 5-membered carbocyclic ring, examples include a cyclopentane, cyclopentene or cyclopentadiene fused nucleus. When Y forms a 5-membered heterocyclic ring, examples include a fused pyrrole, isopyrrole, imidazole, isoimidazole, pyrazole, pyrrolidine, pyrroline, imidazolidine, imidazoline, pyrazolidine, pyrazoline, isothiazole, isoxazole, furazan, furan, thiophene, 1,2,3-triazole, 1,2,4-triazole, dithiole, oxathiole, isoxazole, oxazole, thiazole, isothiazole, oxadiazole, oxatriazole, dioxazole, oxathiazole, and the like ring structures.

When Y forms a 6-membered carbocyclic ring, examples include a fused cyclohexane, cyclohexene or benzene nucleus, optionally substituted with additional fused rings, thus forming, for example, naphthalene, anthracene, phenanthrene, benzonaphthene, and the like ring systems. When Y forms a 6-membered heterocyclic ring, examples include a py-idine, pyrazine, pyrimidine, pyridazine, pyran, pyrone, dioxin, piperidine, piperazine, morpholine, triazine, oxazine, isoxazine, oxathiazine, oxadiazine, and the like rings.

In a preferred embodiment, however, Y has at least one site of unsaturation. Even more preferably, Y represents the atoms necessary to form a fused benzene or naphthalene ring. Y may be unsubstituted or substituted with a non-hydrogen non-interfering substituent.

Possible substituents of Y include any substituent that does not interfere with the reactions and purposes of the invention. Examples include, without limitation, straight or branched chain alkyl groups, such as methyl, ethyl, propyl, butyl, pentyl, hexyl, isopropyl, isobutyl, tert-butyl, n-pentyl, 2-methylpentyl, 2-methylhexyl, dodecyl, octadecyl and the like; straight or branched chain alkenyl groups, such as ethenyl, propenyl, butenyl, pentenyl, 2-methylpentenyl, vinyl, isopropenyl, 2,2-dimethyl-1-propenyl, decenyl, hexadecenyl and the like; straight or branched chain alkynyl groups, such as ethynyl, propynyl, butynyl, pentynyl, hexynyl, heptynyl, octynyl and the like; cycloalkyl groups, such as cyclobutyl, cyclopentyl, cyclohexyl, cycloheptyl, cyclooctyl, cyclononyl, cyclodecyl and the like; cycloalkenyl groups, such as cyclopropenyl, cyclopentadienyl, cyclohexenyl, cyclooctenyl and the like; aralkyl groups, such as benzyl, 3-(1)-naphthyl-1-propyl, p-halobenzyl, p-ethylbenzyl, 1-phenyl-1-propyl, 3-pyridinyl-1-propyl, 1-phenyl-2-sec-butyl, 4-phenyl-4-methyl-1-pentyl and the like;

aryl groups such as phenyl, naphthyl, indenyl, azulenyl, fluorenyl, anthracenyl, indolyl, isoindolyl, indolinyl, benzofuranyl, benzothiophenyl, indazolyl, benzamidazolyl, benzathiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl and the like;

alkoxy groups such as methoxy, ethoxy, sec-propoxy, tert-butoxy, pentoxy, nonoxy and the like; alkenoxy, such as ethenoxy, 2-propenoxy, 3-butenoxy, 2,2-dimethyl-3-butenoxy, 1-hexenoxy, 3-octenoxy, 2-nonenoxy and the like; aryloxy, such as phenoxy, naphthoxy, pyridinoxy and the like; aralkyloxy groups, such as benzyloxy, 1-naphthyl-2-ethoxy and the like; alkanoyl groups such as formyl, acetyl, propanoyl, butanoyl, pentanoyl, benzoyl and the like; haloalkyl groups, such as trifluoromethyl; non-aromatic heterocyclic groups; and other groups, such as hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, sulfhydryl, halo and the like.

Possible substituents on the above-described aryl groups can be any non-interfering substituent. However, preferred substituents include, without limitation, alkyl, alkenyl, alkoxy, phenoxy, benzyloxy, cycloalkyl, cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, sulfhydryl, halo, haloalkyl, and aryl.

Preferably, when Y is substituted with a non-hydrogen, non-interfering substituent, the substituent is selected from the group consisting of —$NO_2$, halo such as chloro or bromo, —OR or —$NHR^1$, where $R^1$ is hydrogen or lower alkyl.

In another preferred embodiment, Y is optionally substituted with a non-interfering substituent that bridges two or more of the fused rings of the compound. Such a compound may have, for example, a tetracyclic structure of the formula:

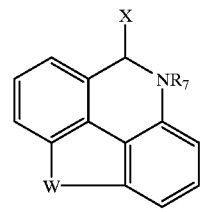

where W is —O—, —S—, or —$NR^1$ where $R^1$ is hydrogen or lower alkyl. Preferably, $R^1$ is lower alkyl, as described above. In yet another embodiment, Y can be substituted with two or more non-hydrogen substituents which, taken together, themselves form an additional fused 5- or 6-membered ring, such as a fused cyclopentyl, cyclopentadiene, benzene, cyclohexene, or cyclohexane ring.

Z in formula I can be
  (i) —$CHR^2CHR^3$—;
  (ii) —$R^6C{=}CR^3$—;
  (iii) —$R^2C{=}N$—;
  (iv) —$CR^2(OH)$—$NR^7$—; or
  (v) —C(O)—$NR^7$—.

Preferably, Z is —$CHR^2CHR^3$—, —$R^6C{=}CR^3$— or —$R^2C{=}N$—.

When Z is —$CHR^2CHR^3$—, $R^2$ is in the meta-position and $R^3$ is in the ortho-position relative to the ring nitrogen of formula I. When Z is —$R^6C{=}CR^3$—, $R^6$ is meta to the ring nitrogen.

$R^2$ and $R^3$ in formulas (i)–(v) above can be, independently, hydrogen; alkyl, such as methyl, ethyl, isopropyl, tert-butyl, n-pentyl, sec-octyl, dodecyl and the like; aryl, such as phenyl; or aralkyl, such as benzyl, 1-naphthylmethyl, and p-halo benzyl.

In formula (ii) (—$R^6C{=}CR^3$—), $R^6$ and $R^3$, independently can be hydrogen, lower alkyl as described above, aryl as described above, aralkyl as described above, halo such as chlorine and bromine, —$NO_2$, —$COOR^7$ or —$NR^7R^8$. When $R^3$ is —$NR^7R^8$, $R^8$ is independently hydrogen or $C_1$–$C_9$ alkyl. Examples of useful $C_1$–$C_9$ alkyl groups for $R^8$ include, without limitation, methyl, ethyl, isopropyl, tert-butyl, n-pentyl, n-hexyl, heptenyl, sec-octyl, and nonyl. Preferably, however, $R^8$ is lower alkyl as described above.

Alternatively, $R^3$ and $R^6$, taken together, can form a fused aromatic, mono-, bi- or tricyclic, carbocyclic or heterocyclic ring, wherein each individual ring has 5–6 ring member atoms. Examples of such rings include a fused pyrrole, isopyrrole, imidazole, isoimidazole, triazole, pyrazole, pyridine, thiophene, furan, thiazole, isothiazole, oxazole, isoxazole, oxadiazole, benzene, naphthalene, acridine, pyran, pyrone, pyrazine, pyrimidine, pyridazine, or triazine groups. When Z is —$R^6C{=}CR^3$— where $R^6$ and $R^3$, taken together, form a fused aromatic ring, the ring formed is preferably substituted with one or more non-hydrogen non-interfering substituents, as described above for Y. Particularly preferred substituents are selected from the group consisting of halo such as chloro and bromo, amino and nitro.

In the compound of the invention, the multicyclic nuclear ring structure formed by Y and Z is preferably one of the following:

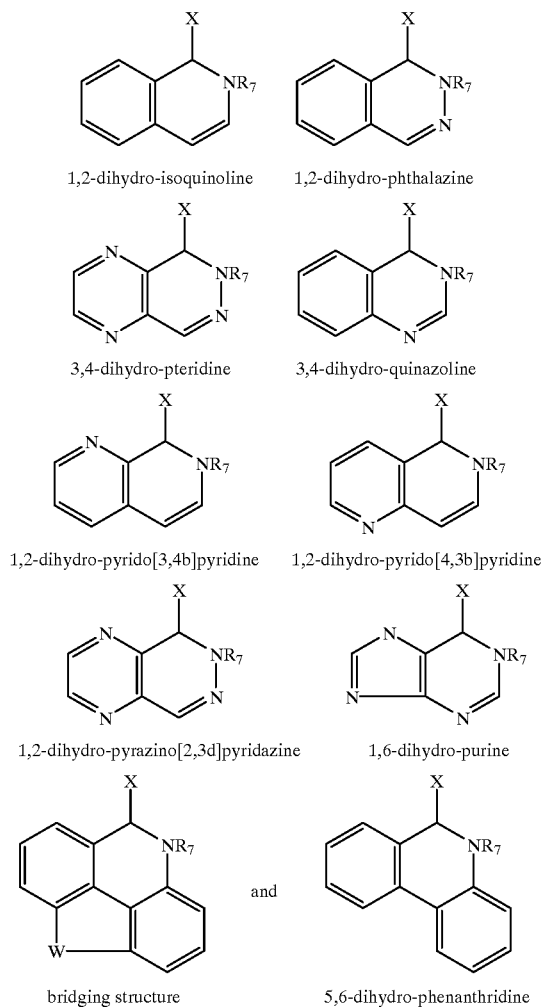

wherein W is as defined as above, or the pharmaco-logically acceptable base or acid addition salts, prodrug, metabolite, optical isomer or stereoisomer thereof. Preferably, the compound of formula I has an isoquinoline, pteridine, phenanthridine, phthalazine, quinazoline nucleus or the tetracyclic bridging structure shown above. Most preferably, the compound has a phenanthridine nucleus.

The following specific examples of oxo-substituted compounds of formula I, as shown below in TABLE I, are illustrative of useful embodiments of the invention and are not to be construed as limiting the invention thereto.

TABLE I

I

| Compound No. | X | Y | Z |
|---|---|---|---|
| 1 | OH | (ring) | —$CH_2$—$CH_2$— |
| 2 | O | (ring) | —CH—$CH_2$—<br>$CH_3$ |
| 3 | OH | (ring) | —CH—$CH_2$—<br>$CH_3$ |
| 4 | O | (O-ring) | —CH—$CH_2$—<br>$C_6H_5$ |
| 5 | OH | (O-ring) | —CH—$CH_2$—<br>$C_6H_5$ |
| 6 | O | (S-ring) | —CH—$CH_2$—<br>$CH_2$—$C_6H_5$ |
| 7 | OH | (S-ring) | —CH—$CH_2$—<br>$CH_2$—$C_6H_5$ |
| 8 | O | (NH-N ring) | —CH—$CH_2$—<br>CH<br>$CH_3$ $CH_3$ |
| 9 | OH | (NH-N ring) | —CH—$CH_2$—<br>CH<br>$CH_3$ $CH_3$ |
| 10 | O | (N-N ring) | —CH—$CH_2$—<br>$CH_3$—C—$CH_3$<br>$CH_3$ |
| 11 | OH | (N-N ring) | —CH—$CH_2$—<br>$CH_3$—C—$CH_3$<br>$CH_3$ |

TABLE I-continued

Structural formula I with substituents X, Y, Z, and NR⁷ on a ring system.

| Compound No. | X | Y | Z |
|---|---|---|---|
| 12 | =O | -NH-CH=CH- | -C(C₂H₅)=CH- |
| 13 | -OH | -NH-CH=CH- | -C(C₂H₅)=CH- |
| 14 | =O | -N=N-NH- | -C(C₆H₅)=CH- |
| 15 | -OH | -N=N-NH- | -C(C₆H₅)=CH- |
| 16 | =O | -N=CH-O- | -C(CH₂-C₆H₅)=CH- |
| 17 | -OH | -N=CH-O- | -C(CH₂-C₆H₅)=CH- |
| 18 | =O | -N=CH-S- | -C(Cl)=CH- |
| 19 | -OH | -N=CH-S- | -C(Cl)=CH- |
| 20 | =O | cyclohexene | -C(Br)=CH- |
| 21 | -OH | cyclohexene | -C(Br)=CH- |
| 22 | =O | cyclohexane | -C(NH-C₂H₅)=CH- |
| 23 | -OH | cyclohexane | -C(NH-C₂H₅)=CH- |
| 24 | =O | -O-CH=CH-CH=CH- | -CH=N- |
| 25 | -OH | -O-CH=CH-CH=CH- | -CH=N- |
| 26 | =O | -O-CH=CH-CH=CH- | -C(CH(CH₃)₂)=N- |
| 27 | -OH | -O-CH=CH-CH=CH- | -C(CH(CH₃)₂)=N- |
| 28 | =O | -N=CH-CH=CH- | -CH(OH)-NH- |
| 29 | -OH | -N=CH-CH=CH- | -CH(OH)-NH- |
| 30 | =O | -N=N-CH=CH- | 2,3-dimethylphenyl |
| 31 | -OH | -N=N-CH=CH- | 2,3-dimethylphenyl |
| 32 | =O | -N=CH-CH=N- | -CO-NH- |

TABLE I-continued

| Compound No. | X | Y | Z |
|---|---|---|---|
| 33 | OH | pyrazine (N=CH-CH=N) | —CO—NH— |
| 34 | O | pyrazine | —CO—N(C₂H₅)— |
| 35 | OH | pyrazine | —CO—N(C₂H₅)— |
| 36 | O | piperazine (N-CH₂-CH₂-N) | 3,4-dimethylthiophene |
| 37 | OH | piperazine | 3,4-dimethylthiophene |
| 38 | O | 1,2,4,5-tetrazine | 2,3-dimethylphenyl |
| 39 | OH | 1,2,4,5-tetrazine | 2,3-dimethylphenyl |
| 40 | O | morpholine-derived (N=CH-O-CH₂) | 3,4-dimethylpyridine |
| 41 | OH | morpholine-derived | 3,4-dimethylpyridine |
| 42 | O | morpholine-derived | —CH₂—CH₂— |
| 43 | OH | morpholine (N-CH₂-CH₂-O-CH₂) | —CH₂—CH₂— |
| 44 | O | phenyl | 3,4-dimethyl-5-aminophenyl |
| 45 | OH | phenyl | 3,4-dimethyl-5-aminophenyl |
| 46 | O | phenyl | 3,4-dimethyl-5-bromophenyl |
| 47 | OH | phenyl | 3,4-dimethyl-5-bromophenyl |

TABLE I-continued

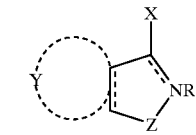

| Compound No. | X | Y | Z |
|---|---|---|---|
| 48 | =O |  (phenyl-NO2) | 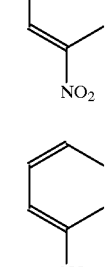 (methyl-phenyl-NH2) |
| 49 | OH | 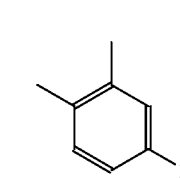 (phenyl-NO2) | 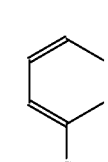 (methyl-phenyl-NH2) |
| 50 | =O | 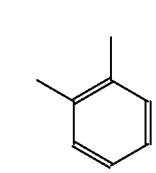 (phenyl-SMe) | 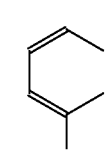 (methyl-phenyl) |
| 51 | OH | 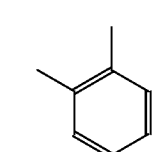 (phenyl-SMe) | 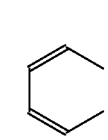 (methyl-phenyl-Br) |
| 52 | =O | 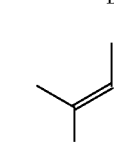 (phenyl) | C(CH3)=CH-NO2 |
| 53 | =O | 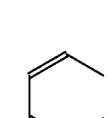 (phenyl) | C(CH3)=CH-COOH |
| 54 | OH | 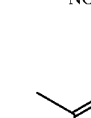 (phenyl) | C(CH3)=CH-COOH |
| 55 | =O | 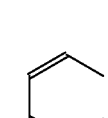 (phenyl-NO2) | CH=CH-CH3 |

TABLE I-continued

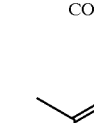

| Compound No. | X | Y | Z |
|---|---|---|---|
| 56 | OH | (phenyl-NO2) | CH=CH-CH3 |
| 57 | =O | (phenyl) | C(CH3)=CH-COOCH3 |
| 58 | OH | (phenyl) | C(CH3)=CH-COOCH3 |
| 59 | =O | (phenyl) | (methyl-phenyl-Cl) |
| 60 | OH | (phenyl) | (methyl-phenyl-Cl) |
| 61 | =O |  (Cl-substituted) | (methyl-phenyl-Cl) |
| 62 | OH | 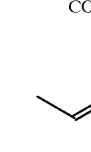 (Cl-substituted) | (methyl-phenyl-Cl) |

TABLE I-continued

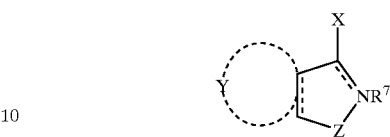

| Compound No. | X | Y | Z |
|---|---|---|---|
| 63 | =O | (cyclohexadiene) | 2-methyl-3-bromo-6-nitrophenyl |
| 64 | OH | (cyclohexadiene) | 2-methyl-3-bromo-6-nitrophenyl |
| 65 | =O | (cyclohexadiene) | —C(C6H5)=CH— |
| 66 | OH | (cyclohexadiene) | —C(C6H5)=CH— |
| 67 | =O | (thiophene) | —CH=CH— |
| 68 | OH | (thiophene) | —CH=CH— |
| 69 | =O | (cyclohexadiene) | 3-methylnaphthalen-2-yl |
| 70 | OH | (cyclohexadiene) | 3-methylnaphthalen-2-yl |
| 71 | =O | —C(Cl)=CH— | 2-methylphenyl |

Also included are the pharmacologically acceptable base or acid addition salts, prodrug, metabolite, optical isomer or stereoisomer thereof.

Particularly preferred compounds of TABLE I of the invention are Compounds Nos. 46, 48, 50, 52, 59, 61, 63, 69 and 71. Most preferably, of this group, the compound of the invention is Compound No. 59.

Another preferred group of compounds of formula I is as shown below in TABLE II:

TABLE II

| X | Y | Z | Compound Structure |
|---|---|---|---|
| =O | (furan) | —CH(C6H5)—CH2— | (furo-pyridinone with C6H5 and NCH3) |

TABLE II-continued

| X | Y | Z | Compound Structure |
|---|---|---|---|
| OH | (cyclopentene-like fragment) | —CH₂—CH₂— | (bicyclic structure with OH and NH) |
| O (=) | S, N (thiazole-like) | —C=CH— with Cl | (thiazole-fused ring with NC₂H₅ and Cl) |
| O (=) | N=N-H (pyrazole-like) | —CH—CH₂— with CH(CH₃)CH₃ | (pyrazole-fused ring with NC₂H₅ and CH(CH₃)₂) |
| O (=) | (cyclopentene fragment) | —CH—CH₂— with CH₃ | (bicyclic structure with NCH₃ and CH₃) |
| O (=) | S (thiophene-like) | —C=CH— with CH₂—C₆H₅ | (thiophene-fused ring with NC₅H₁₁ and CH₂—C₆H₅) |
| O (=) | O (furan-like) | —CH₂=N— | (pyranopyridazinone-like ring with NCH₃) |

Another example of a pre-erred class of compounds as is shown below in TABLE III as formula II:

TABLE III

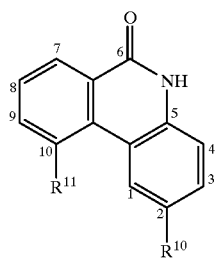

| R$^{11}$ | R$^{10}$ | Compound Name |
|---|---|---|
| —CH$_3$ | —Cl | 5(H)2-chloro-10-methylphenanthridin-6-one |
| —CH$_3$ | —NO$_2$ | 5(H)2-nitro-10-methylphenanthridin-6-one |
| —NH$_2$ | —Cl | 5(H)2-chloro-10-aminophenanthridin-6-one |
| —NH$_2$ | —NO$_2$ | 5(H)2-nitro-10-aminophenanthridin-6-one |
| —NO$_2$ | —Cl | 5(H)2-chloro-10-nitrophenanthridin-6-one |
| —NO$_2$ | —NO$_2$ | 5(H)2,10-dinitrophenanthridin-6-one |
| —OH | —Cl | 5(H)2-chloro-10-hydroxyphenanthridin-6-one |
| —OH | —NO$_2$ | 5(H)2-nitro-10-hydroxyphenanthridin-6-one |
| —Br | —Cl | 5(H)2-chloro-10-bromophenanthridin-6-one |
| —Br | —NO$_2$ | 5(H)2-nitro-10-bromophenanthridin-6-one |
| —NO | —Cl | 5(H)2-chloro-10-nitrosophenanthridin-6-one |

Yet another group of preferred compounds have formula III and are exemplified below in TABLE IV:

TABLE IV

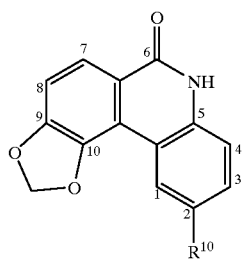

| R$^{10}$ | Compound Name |
|---|---|
| —Cl | 5(H)2-chloro-9,10-methlenedihydroxy-phenanthridin-6-one |
| —NO$_2$ | 5(H)2-nitro-9,10-methlenedihydroxy-phenanthridin-6-one |

Compounds of the present invention may possess one or more asymmetric center(s) and thus can be produced as mixtures (racemic and non-racemic) of stereoisomers, or as individual R- and S- stereoisomers. The individual stereoisomers may be obtained by using an optically active starting material, by resolving a racemic or non-racemic racemic mixture of an intermediate at some appropriate stage of synthesis, or by resolving a compound of formula I.

The term "isomers" refer to compounds having the same number and kind of atoms, and hence, the same molecular weight, but differing in respect to the arrangement or configuration of the atoms. "Stereoisomers" or "optical isomers" are isomers that differ only in the arrangement of atoms in space. "Enantiomers" are a pair of stereoisomers that are non-superimposable mirror images of each other. "Diastereoisomers" are stereoisomers which are not mirror images of each other. "Racemic mixture" means a mixture containing equal or roughly equal parts of individual enantiomers. "Non-racemic mixtures" is a mixture containing unequal parts of individual enantiomers or stereoisomers.

The compounds of the invention may be useful in a free base form, in the form of pharmaceutically acceptable base salts, in the form of pharmaceutically acceptable acid addition salts, in the form of pharmaceutically acceptable prodrugs, in the form of pharmaceutically acceptable metabolites, in the form of pharmaceutically acceptable optical isomers or stereoisomers or in the free acid form. These eight forms are all within the scope of the invention. In practice, the use of these forms amounts to use of the neutral compound.

"Pharmaceutically acceptable salt" refers to a salt of the inventive compounds which possesses the desired pharmacological activity and which is neither biologically nor otherwise undesirable. Pharmaceutically acceptable salts within the scope of this invention are those derived from mineral acids such as hydrochloric and sulfuric acid; and organic acids such as ethanesulfonic acid, benzenesulfonic acid, p-toluenesulfonic acid, and the like, respectively giving the hydrochloride, sulfonate, ethanesulfonate, benzenesulfonate, p-toluene-sulfonate and the like.

Organic acids can be used to produce salts such as acetate, adipate, alginate, aspartate, benzoate, benzenesulfonate, p-toluenesulfonate, bisulfate, sulfamate, butyrate, citrate, camphorate, camphor-sulfonate, cyclopentane propionate, digluconate, dodecylsulfate, ethanesulfonate, fumarate, gluco-heptanoate, glycerophosphate, hemisulfate heptanoate, hexanoate, 2-hydroxyethanesulfonate, lactate, maleate, methanesulfonate, 2-naphthalenesulfonate, nicotinate, oxalate, tosylate, and undecanoate. Inorganic acids can be used to produce salts such as hydrochloride, hydro-bromide, hydroiodide, and thiocyanate.

Examples of suitable base salts include hydroxides, carbonates, and bicarbonates of ammonia, alkali metal salts such as sodium, lithium and potassium salts, alkaline earth metal salts such as calcium and magnesium salts, aluminum salts, and zinc salts.

Salts may also be formed with suitable organic bases. Organic bases suitable for the formation of pharmaceutically acceptable base addition salts of the compounds of the present invention include those that are non-toxic and strong enough to form such salts. For purposes of illustration, the class of such organic bases may include mono-, di-, and trialkylamines, such as methylamine, dimethylamine, triethylamine and dicyclohexylamine; mono-, di- or trihydroxyalkylamines, such as mono-, di-, and triethanolamine; amino acids, such as arginine and lysine; guanidine; N-methylglucosamine; N-methyl-glutamine; L-glutamine; N-methylpiperazine; morpholine; ethylenediamine; N-benzylphenethylamine; (trihydroxy-methyl)aminoethane; and the like. See, for example, "Pharmaceutical Salts," *J. Pharm. Sc.*, 66:1, 1–19 (1977). Accordingly, basic nitrogen-containing groups can be quaternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The acid addition salts of the basic compounds may be prepared either by dissolving the free base of a PARP inhibitor in an aqueous or an aqueous alcohol solution or other suitable solvent containing the appropriate acid or base, and isolating the salt by evaporating the solution. Alternatively, the free base of the PARP inhibitor may be reacted with an acid, as well as reacting the PARP inhibitor having an acid group thereon with a base, such that the reactions are in an organic solvent, in which case the salt separates directly or can be obtained by concentrating the solution.

The compounds of the invention exhibit pharmacological activity and are, therefore, useful as pharmaceuticals. In particular, the compounds exhibit central nervous and cardiac vesicular system activity.

After entry into the body, most drugs are substrates for chemical reactions that may change their physical properties and biologic effects. These metabolic conversions, which usually affect the polarity of the compound, alter the way in which drugs are distributed in and excreted from the body. However, in some cases, metabolism of a drug is required for therapeutic effect. For example, anticancer drugs of the antimetabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products are more polar than the parent drugs, although a polar drug does sometimes yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilid is given to a person, the successive metabolites peak and decay in the plasma sequentially. During the first hour, acetanilid is the principal plasma component. In the second hour, as the acetanilid level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

The reactions involved in drug metabolism are often classified into two groups, as shown in the TABLE V. Phase I (or functionalization) reactions generally consist of (1) oxidative and reductive reactions that alter and create new functional groups and (2) hydrolytic reactions that cleave esters and amides to release masked functional groups. These changes are usually in the direction of increased polarity.

Phase II reactions are conjugation reactions in which the drug, or often a metabolite of the drug, is coupled to an endogenous substrate, such as glucuronic acid, acetic acid, or sulfuric acid.

TABLE V

Phase I Reactions (functionalization reactions):

| | |
|---|---|
| (1) | Oxidation via the hepatic microsomal P450 system: |
| | Aliphatic oxidation |

TABLE V-continued

| | |
|---|---|
| | Aromatic hydroxylation |
| | N-Dealkylation |
| | O-Dealkylation |
| | S-Dealkylation |
| | Epoxidation |
| | Oxidative deamination |
| | Sulfoxide formation |
| | Desulfuration |
| | N-Oxidation and N-hydroxylation |
| | Dehalogenation |
| (2) | Oxidation via non-microsomal mechanisms: |
| | Alcohol and aldehyde oxidation |
| | Purine oxidation |
| | Oxidative deamination (monoamine oxidase and diamine oxidase) |
| (3) | Reduction: |
| | Azo and nitro reduction |
| (4) | Hydrolysis: |
| | Ester and amide hydrolysis |
| | Peptide bond hydrolysis |
| | Epoxide hydration |
| Phase II Reactions (conjugation reactions): | |
| (1) | Glucuronidation |
| (2) | Acetylation |
| (3) | Mercapturic acid formation |
| (4) | Sulfate conjugation |
| (5) | N-, O-, and S-methylation |
| (6) | Trans-sulfuration |

Typically, the compounds of formula I inhibitors used in the composition of the invention will have an $IC_{50}$ for inhibiting poly(ADP-ribose)polymerase in vitro of 100 $\mu$M or lower, preferably 25 $\mu$M or lower, more preferably 12 $\mu$M or lower and, even more preferably, 12 mM or lower.

Synthesis of Compounds

Many compounds inhibiting PARP activity can be synthesized by known methods from starting materials that are known, are themselves commercially available, or may be prepared by methods used to prepare corresponding compounds in the literature. See, for example, Suto et al., "Dihydroisoquinolinones: The Design and Synthesis of a New Series of Potent Inhibitors of Poly(ADP-Ribose) Polymerase", *Anticancer Drug Des.*, 7:107–17 (1991), which discloses processes for synthesizing a number of different PARP inhibitors.

Preferred building blocks for synthesizing the compounds of formula I where X is double-bonded oxygen are phenanthridinones. As an example, the (5H)phenanthridin-6-one compounds of the invention can be prepared by reacting a compound of formula IV:

IV

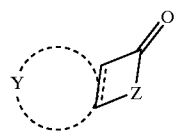

with a nitrogen-insertion agent, such as a combination of $NaN_3$ and $H_2SO_4$, to form a compound of formula V:

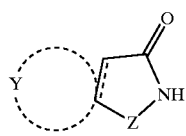

For example, the Schmidt method can be used in a conventional manner to make a (5H)phenanthridin-6-one from a fluorene-9-one as illustrated below:

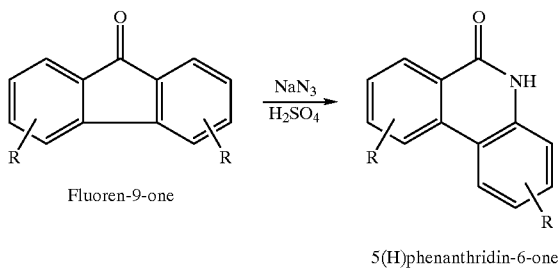

Fluoren-9-one

5(H)phenanthridin-6-one

In this example, the fluoren-9-one is generically substituted. Such fluoren-9-one starting derivatives are known in the chemistry literature and are accessible by processes known to one skilled in the art. Phenanthrididones can also be prepared through an intramolecular Heck reaction analogous to that disclosed by Chide et al., *Tetrahedron Lett.*, 32:35, 4525–28 (1991).

Other methods that may be useful in preparing the compounds of the invention include, but are not limited to:

I. the Smith reaction of Respondly et al., *Acad. Sci. Paris, Ser. C,* (1967);

II. the photocyclization method described by Ninomiya et al., *Tetrahedron Lett.*, 4451 (1970) and Ichiya et al., *J. Chem. Soc.*, 1:2257 (1973);

III. isocyanate intramolecular cycloaddition reactions, such as that found in:
  (a) Balazs et al., Synthesis, 1373 (1995)); Banwell et al., *J. Chem. Soc.*, 1:3515 (1994);
  (b) Migachev et al., *J. Org. Chem. USSR* (Eng. Trans.), 20:8, 1565–71 (1984) and *Zh. Org. Khim.*, 20:8, 1718–24 (1984);
  (c) Migachev et al., *Chem. Heterocycl. Compd.* (Eng. Trans.), 17:3, 289–94 (1981) and *Khim. Geterotsikl. Soedin.*, 17:3, 388–91 (1981);
  (d) Migatschew et al., *J. Gen. Chem. USSR* (Eng. Trans.); 48, 2116, (1978));
  (e) Chandler et al., *Aust. J. Chem.*, 20, 2037–44 (1967));
  (f) Ruediger et al., *Can. J. Chem*, 64, 577–9 (1986).

The disclosures of the above-listed reference are hereby incorporated by reference. Other variations and modifications of the synthetic pathways described above will be obvious to those skilled in the art.

Pharmaceutical Compositions

A further aspect of the present invention is directed to a pharmaceutical composition comprising a pharmaceutically acceptable carrier or a diluent and a compound of formula I or a pharmaceutically acceptable salt, prodrug, metabolite, optical isomer or stereoisomer thereof (hereinafter, "compound of formula I"). Preferably, the compound of formula I is present in an amount effective for inhibiting PARP activity.

The formula I compounds of the invention are useful in the manufacture of pharmaceutical formulations comprising an effective amount thereof in conjunction or admixture with excipients or carriers suitable for either enteral or parenteral application. As such, formulations of the present invention suitable for oral administration may be in the form of discrete units such as capsules, cachets, tablets, troche or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The composition will usually be formulated into a unit dosage form such as a tablet, capsule, aqueous suspension or solution. Such formulations typically include a solid, semisolid, or liquid carrier. Exemplary carriers include lactose, cornstarch, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

Preferred formulations are tablets and gelatin capsules comprising the active ingredient together with a) diluents, e.g., lactose, dried cornstarch, dextrose, sucrose, mannitol, sorbitol, cellulose, and/or glycine; and/or b) lubricants, e.g., silica, talcum, stearic acid, its magnesium or calcium salt, and polyethylene glycol. Tablets may also contain binders, e.g., magnesium aluminum silicate, starch paste, gelatin, tragacanth, methyl cellulose, sodium carboxymethylcellulose, or polyvinyl-pyrrolidone. If desired, tablets may also contain disintegrants, e.g., starches, agar, alginic acid, or its sodium salt, or effervescent mixtures; and/or absorbents, colorants, flavors, and sweeteners. Aqueous suspensions may contain emulsifying and suspending agents combined with the active ingredient. The oral dosage forms may further contain sweetening and/or flavoring and/or coloring agents.

These compositions may be sterilized and/or contain adjuvants, such as preserving, stabilizing, welling or emulsifying agents; solution promoters; salts for regulating the osmotic pressure, and/or buffers. In addition, they may also contain other therapeutically valuable substances. These compositions are prepared according to conventional mixing, granulating, or coating methods, respectively.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active or dispersing agent. Molded tablets may be made by molding, in a suitable machine, a mixture of the powdered active ingredient and a suitable carrier moistened with an inert liquid diluent.

When administered parenterally, the composition will normally be in a unit dosage, sterile injectable form (aqueous isotonic solution, suspension or emulsion) with a pharmaceutically acceptable carrier. Such carriers are preferably non-toxic, parenterally-acceptable and contain non-therapeutic diluents or solvents. Examples of such carriers include water; aqueous solutions, such as saline (isotonic sodium chloride solution), Ringer's solution, dextrose solution, and Hanks' solution; and nonaqueous carriers, such as 1,3-butanediol, fixed oils (e.g., corn, cottonseed, peanut, sesame oil, and synthetic mono-or di-glyceride), ethyl oleate, and isopropyl myristate. oleaginous suspensions can be formulated according to techniques known in the art using suitable dispersing or wetting agents and suspending agents. Among the acceptable solvents or suspending mediums are sterile fixed oils. For this purpose, any bland fixed oil may be used. Fatty acids, such as oleic acid and its glyceride derivatives, including olive oil and castor oil, especially in their polyoxyethylated forms, are also useful in the preparation of injectables. These oil solutions or suspensions may also contain long-chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., antioxidants, buffers and preservatives.

When administered rectally, the composition will usually be formulated into a unit dosage form such as a suppository or cachet. These compositions can be prepared by mixing the compound with suitable non-irritating excipients that are solid at room temperature, but liquid at rectal temperature, such that they will melt in the rectum to release the compound. Common excipients include cocoa butter, beeswax and polyethylene glycols or other fatty emulsions or suspensions.

Moreover, the compounds may be administered topically, especially when the conditions addressed for treatment involve areas or organs readily accessible by topical application, including neurological disorders of the eye, the skin or the lower intestinal tract.

For topical application to the eye, or ophthalmic use, the compounds can be formulated as micronized suspensions in isotonic, pH-adjusted sterile saline or, preferably, as a solution in isotonic, pH-adjusted sterile saline, either with or without a preservative such as benzylalkonium chloride. Alternatively, the compounds may be formulated into ointments, such as petrolatum.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene compound, polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

Formulations suitable for nasal or buccal administration, (such as self-propelling powder dispensing formulations), may comprise about 0.1% to about 5% w/w of the active ingredient or, for example, about 1% w/w of the same. In addition, some formulations can be compounded into a sublingual troche or lozenge.

The formulations may conveniently be presented in unit dosage form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

The composition of the invention is preferably administered as a capsule or tablet containing a single or divided dose of the inhibitor, or as a sterile solution, suspension, or emulsion, for parenteral administration in a single or divided dose.

In another preferred embodiment, the PARP inhibitor compounds of the invention can be prepared in lyophilized form. In this case, 1 to 100 mg of a PARP inhibitor may be lyophilized in individual vials, together with a carrier and a buffer, such as mannitol and sodium phosphate. The compound may be reconstituted in the vials with bacteriostatic water before administration.

In yet another preferred embodiment, the carrier is a solid biodegradable polymer with appropriate time release characteristics. The composition of the invention may then be molded into a solid implant suitable for providing efficacious concentrations of the PARP inhibitors over a prolonged period of time without the need for frequent re-dosing.

The PARP inhibitors are used in the composition in amounts that are therapeutically effective. While the effective amount of the PARP inhibitor will depend on the particular inhibitor and the dosage form being used, amounts of the PARP inhibitor varying from about 0.1% to 75%, preferably about 1% to 65% and, even more preferably, about 1% to 50%, have been easily incorporated into liquid or solid carrier delivery. systems.

Methods of Effecting Neuronal Activity

According to the methods of the invention, an effective therapeutic amount of the compounds and compositions described above are administered to animals to effect a neuronal activity, preferably one that is not mediated by NMDA neurotoxicity. Such neuronal activity may consist of stimulation of damaged neurons, promotion of neuronal regeneration, prevention of neurodegeneration and treatment of a neurological disorder. Accordingly, the present invention further relates to a method of effecting a neuronal activity in an animal, comprising administering an effective amount of the compound of formula I to the animal. Further, the compounds of the invention inhibit PARP and, thus, are believed to be useful for treating neural tissue damage, particularly damage resulting from cerebral ischemia and reperfusion injury or neurodegenerative diseases in mammals.

The term "nervous tissue" refers to the various components that make up the nervous system including, without limitation, neurons, neural support cells, glia, Schwann cells, vasculature contained within and supplying these structures, the central nervous system, the brain, the brain stem, the spinal cord, the junction of the central nervous system with the peripheral nervous system, the peripheral nervous system, and allied structures.

The term "neural tissue damage resulting from ischemia and reperfusion injury and neurodegenerative diseases" includes neurotoxicity, such as seen in vascular stroke and global and focal ischemia.

The term "neurodegenerative diseases" includes Alzheimer's disease, Parkinson's disease and Huntington's disease.

The term "nervous insult" refers to any damage to nervous tissue and any disability or death resulting therefrom. The cause of nervous insult may be metabolic, toxic, neurotoxic, iatrogenic, thermal or chemical, and includes without limitation, ischemia, hypoxia, cerebrovascular accident, trauma, surgery, pressure, mass effect, hemorrhage, radiation, vasospasm, neurodegenerative, disease, infection, Parkinson's disease, amyotrophic lateral sclerosis (ALS), epilepsy, myelination/demyelination process, cognitive disorder, glutamate abnormality and secondary effects thereof.

The term "neuroprotective" refers to the effect of reducing, arresting or ameliorating nervous insult, and protecting, resuscitating or reviving nervous tissue which has suffered nervous insult.

The term "preventing neurodegeneration" includes the ability to prevent neurodegeneration in patients diagnosed as having a neurodegenerative disease or who are at risk of developing a neurodegenerative disease. The term also encompasses preventing further neurodegeneration in patients who are already suffering from or have symptoms of a neurodegenerative disease.

Examples of neurological disorders that are treatable by the method of using the present invention include, without limitation, trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barré syndrome; Alzheimer's disease; Huntington's disease and Parkinson's disease.

The method of the present invention is particularly useful for treating a neurological disorder selected from the group consisting of: peripheral neuropathy caused by physical injury or disease state, traumatic brain injury, physical damage to the spinal cord, stroke associated with brain damage, demyelinating diseases and neurological disorders related to neurodegeneration. Examples of demyelinating diseases include multiple sclerosis. Examples of neurological disorders relating to neurodegeneration include Alzheimer's disease, Parkinson's disease and amyotrophic lateral sclerosis (ALS).

The term "treating" refers to:
(i) preventing a disease, disorder or condition from occurring in an animal which may be predisposed to the disease, disorder and/or condition but has not yet been diagnosed as having it;
(ii) inhibiting the disease, disorder or condition, i.e., arresting its development; and
(iii) relieving the disease, disorder or condition, i.e., causing regression of the disease, disorder and/or condition.

Treating Other PARP-related Disorders

The invention further can also be used to treat a cardiovascular disorder in an animal, comprising administering an effective amount of the compound of formula I to the animal. Further, the methods of the invention are believed to be useful for treating cardiovascular tissue damage, particularly damage resulting from cardiac ischemia or caused by reperfusion injury in mammals due to PARP activation.

As used herein, the term "cardiovascular disorders" relates to coronary artery disease, angina pectoris, myocardial infarction, cardiogenic shock, and related conditions that would be known by those of skill in the art or which involve dysfunction of or tissue damage to the heart or vasculature, and especially, but not limited to, tissue damage related to PARP activation.

The term "ischemia" refers to localized tissue anemia due to obstruction of the inflow of arterial blood. Global ischemia occurs when blood flow to the entire brain ceases for a period of time, for example, during cardiac arrest. Focal ischemia occurs when a portion of the brain is deprived of its normal blood supply. Focal ischemia may result from thromboembolytic occlusion of a cerebral vessel, traumatic head injury, edema or brain tumor. Even if transient, both global and focal ischemia can cause widespread neuronal damage.

Although nerve tissue damage occurs over hours or even days following the onset of ischemia, some permanent nerve tissue damage may develop in the initial minutes following cessation of blood flow to the brain. Much of this damage is attributed to glutamate toxicity and secondary consequences of reperfusion of the tissue, such as the release of vasoactive products by damaged endothelium, and the release of cytotoxic products, such as free radicals and leukotrines, by the damaged tissue. Ischemia can also occur in the heart in myocardial infarction and other cardiovascular disorders when the coronary arteries are obstructed as a result of atherosclerosis, thrombi, or spasm.

The methods of the present invention are particularly useful for treating cardiovascular disorders selected from the group consisting of: coronary artery disease such as atherosclerosis, angina pectoris, myocardial infarction, cardiogenic shock and cardiovascular tissue damage.

The methods of the invention can also be used to treat arthritis in an animal; diabetes; septic shock such as endotoxic shock; and inflammatory bowel disorders such as colitis and Crohn's disease.

Further, the methods of the invention can be used to treat cancer in an animal. The compounds of the present invention are "anti-cancer agents", which term also encompasses "anti-tumor cell growth agents" and "anti-neoplastic agents".

For example, the methods of the present invention are particularly useful for treating cancers such as: ACTH-producing tumors, acute lymphocytic leukemia, acute non-lymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, prostate cancer, pancreatic cancer, penis cancer, retirnoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva and Wilm's tumor.

Administration

In the methods of the present invention, the compounds may be administered orally, parenterally, by inhalation spray, topically, rectally, nasally, buccally, sublingually, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraosseous, intraperitoneal, intrathecal, intraventricular, intraspinal, intrasternal or intacranial injection and infusion techniques and by subdural pumps. Invasive techniques are preferred, particularly direct administration to damaged neuronal tissue.

To be effective therapeutically for central nervous system targets, the compounds used in the methods of the present invention should readily penetrate the blood-brain barrier when peripherally administered. Compounds which cannot penetrate the blood-brain barrier, however, can still be effectively administered by an intraventricular route.

The compounds used in the methods of the present invention may be administered by a single dose, multiple discrete doses or continuous infusion. Since the compounds are small, easily diffusible and relatively stable, they are well suited to continuous infusion. Pump means, particularly subcutaneous pump means or as a subdural pump, are preferred for continuous infusion.

For medical use, the amount required of a compound of formula I to achieve a therapeutic affect will vary according to the particular compound administered, the route of administration, the mammal under treatment, and the particular disorder or disease concerned. It is understood that the ordinarily skilled physician or veterinarian will readily be able to determine and prescribe the amount of the compound effective for the desired prophylactic or therapeutic treatment. In so doing, the physician or veterinarian may employ an intravenous bolus followed by an intravenous infusion and repeated administrations, orally or parenterally, as considered appropriate. While it is possible for the compound of formula I to be administered alone, it is preferable to provide it as part of a pharmaceutical formulation.

Doses of the compounds preferably include pharmaceutical dosage units comprising an efficacious quantity of active compound. By an efficacious quantity is meant a quantity sufficient to inhibit PARP and derive the beneficial effects therefrom through administration of one or more of the pharmaceutical dosage units. Preferably, the dose is sufficient to prevent or reduce the effects of vascular stroke or other neurodegenerative diseases.

An exemplary daily dosage unit for a vertebrate host comprises an amount of from about 0.001 mg/kg to about 50 mg/kg. Preferably, dosage levels on the order of about 0.1 mg to about 10,000 mg of the active ingredient compound are useful in the treatment of the above conditions, with even more preferred levels being about 0.1 mg to about 1,000 mg. More preferably, a suitable systemic dose of compound of formula I for a mammal suffering from, or likely to suffer from, any condition as described herein is in the range of about 0.1 to about 100 mg of the compound per kilogram of body weight, and most preferably, from about 1 to about 10 mg/kg of mammal body weight.

The specific dose level for any particular patient will vary depending upon a variety of factors, including the activity of the specific compound employed; the age, body weight, general health, sex and diet of the patient; the time of administration; the rate of excretion; combination of the compound with other drugs; the severity of the particular disease being treated; the form of the drug; and the route of administration. Typically, in vitro dosage-effect results provide useful guidance on the proper doses for patient administration. Studies in animal models are also helpful. The considerations for determining the proper dose levels are well known in the art.

In methods of treating nervous insult (particularly acute ischemic stroke and global ischemia caused by drowning or head trauma), the compounds of the invention can be co-administered with one or more other therapeutic agents, preferably agents that can reduce the risk of stroke (such as aspirin) and, more preferably, agents that can reduce the risk of a second ischemic event (such as ticlopidine).

The compounds and compositions of the invention can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of the compound of the invention, as well as one or more pharmaceutical excipients, such as wetting, emulsifying and pH buffering agents. When the compounds used in the methods of the present invention are administered in combination with one or more other therapeutic agents, specific dose levels for those agents will depend upon considerations such as those identified above for compounds, composition and methods of the invention in general.

TABLE VI below provides known median dosages for selected chemotherapeutic agents that may be administered in combination with the compounds of the invention to treat such diseases as various cancers.

TABLE VI

| CHEMOTHERAPEUTIC AGENT | MEDIAN DOSAGE |
|---|---|
| Asparayinase | 10,000 units |
| Bleomycin Sulfate | 15 units |
| Carboplatin | 50–450 mg |
| Carmustine | 100 mg |
| Cisplatin | 10–50 mg |
| Cladribine | 10 mg |
| Cyclophosphamide (lyophilized) | 100 mg to 2 gm |
| Cyclophosphamide (non-lyophilized) | 100 mg to 2 gm |
| Cytarabine (lyophilized powder) | 100 mg–2 gm |
| Dacarbazine | 100–200 mg |
| Dactinomgcin | 0.5 mg |
| Daunorubicin | 20 mg |
| Diethylstilbestrol | 250 mg |
| Doxorubicin | 10–150 mg |
| Etidronate | 300 mg |
| Etoposide | 100 mg |
| Floxuridine | 500 mg |
| Fludarabine Phosphate | 50 mg |
| Fluorouracil | 500 mg to 5 gm |
| Goserelin | 3.6 mg |
| Granisetron Hydrochloride | 1 mg |
| Idarubicin | 5–10 mg |
| Ifosfamide | 1–3 gm |
| Leucovorin Calcium | 50–350 mg |
| Leuprolide | 3.75–7.5 mg |
| Mechlorethamine | 10 mg |
| Medroxyprogesterone | 1 gm |
| Melphalan | 50 gm |
| Methotrexate | 20 mg to 1 gm |
| Mitomgcin | 5–40 mg |
| Mitoxantrone | 20–30 mg |
| Ondansetron Hydrochloride | 40 mg |
| Paclitaxel | 30 mg |
| Pamidronate Disodium | 30–90 mg |
| Pegaspargase | 750 units |
| Plicamgcin | 2,500 mcgm |
| Streptozocin | 1 gm |
| Thiotepa | 15 mg |
| Teniposide | 50 mg |
| Vinblastine | 10 mg |
| Vincristine | 1–5 mg |
| Aldesleukin | 22 million units |
| Epoetin Alfa | 2,000–10,000 units |
| Filgrastim | 300–480 mcgm |
| Immune Globulin | 500 mg to 10 gm |
| Interferon Alpha-2a | 3–36 million units |
| Interferon Alpha-2b | 3–50 million units |
| Levamisole | 50 mg |
| Octreotide | 1,000–5,000 mcgm |
| Sargramostim | 250–500 mcgm |

For the methods of the present invention, any administration regimen regulating the timing and sequence of delivery of the compound can be used and repeated as necessary to effect treatment. Such regimen may include pretreatment and/or co-administration with additional therapeutic agents.

To maximize protection of nervous tissue from nervous insult, the compounds of the invention should be administered to the affected cells as soon as possible. In situations where nervous insult is anticipated, the compounds should be administered before the expected nervous insult. Such situations of increased likelihood of nervous insult include surgery (carotid endarterectomy, cardiac, vascular, aortic, orthopedic); endovascular procedures such as arterial catheterization (carotid, vertebral, aortic, cardia, renal, spinal, Adamkiewicz); injections of embolic agents;. coils or balloons for hemostasis; interruptions of vascularity for treatment of brain lesions; and predisposing medical conditions such as crescendo transient ischemic attacks, emboli and sequential strokes.

Where pretreatment for stroke or ischemia is impossible or impracticable, it is important to get the compounds of the invention to the affected cells as soon as possible during or after the event. In the time period between strokes, diagnosis and treatment procedures should be minimized to save the cells from further damage and death.

A particularly advantageous mode of administration for a patient diagnosed with acute vascular stroke is by implantation as a subdural pump to deliver the compound(s) of the invention directly to the infarct area of the brain. Even if comatose, it is expected that the patient would recover more quickly that if he or she did not receive the compound. Further, it is expected that residual neurological symptoms and re-occurrence of vascular stroke would be reduced.

Depending on the patient's presenting symptoms and the response to the administration of the compound, the patient may receive the same or a different compound: parenterally, by injection or by intravenous administration; orally, by capsule or tablet; by implantation of a biocompatible, biodegradable polymeric matrix delivery system comprising the compound of formula I; or by direct administration to an infarct area by insertion of a subdural pump or a central line. It is expected that the treatment would alleviate the disorder, either in part or in its entirety and that no or fewer further occurrences of the disorder would develop. It also is expected that the patient would suffer fewer residual symptoms.

Examples of such disorders include, for example, peripheral neuropathy caused by physical injury, peripheral neuropathy caused by disease state, Guillain-Barré syndrome, head trauma, physical damage to the spinal cord, vascular stroke associated with hypoxia and brain damage, focal cerebral ischemia, global cerebral ischemia, cerebral reperfusion injury, a demyelinating disease, multiple sclerosis, a neurological disorder relating to neurodegeneration, Alzheimer's disease, Parkinson's disease, Huntington's disease, .amyotrophic lateral sclerosis (ALS), cardiovascular disease, such as acute coronary artery disease, acute cardiogenic shock, acute myocardial infarction, acute myocardial ischemia, full cardiac and respiratory arrest, septic shock, diabetes, arthritis, inflammatory bowel disorder such as colitis or Crohn's disease, and cancer.

Where the patient is diagnosed with an acute disorder prior to the availability of the compound of formula I, the patient's condition may deteriorate due to the disorder and become a chronic disorder by the time that the compounds of formula I are available. Even if the patient receives the compound after the disorder has become chronic, it is expected that the patient's condition would still improve and stabilize as a result of receiving the compound.

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

EXAMPLE 1

Approximate $IC_{50}$ Data for Selected PARP Inhibitors

The $IC_{50}$ of a PARP inhibitor compound is a PARP assay using purified recombinant human PARP from Trevigen (Gaithersburg, Md.), as follows: The PARP enzyme assay was set up on ice in a volume of 100 microliters consisting of 10 mM Tris-HCl (pH 8.0), 1 mM $MgCl_2$, 28 mM KCl, 28 mM NaCl, 0.1 mg/ml of herring sperm DNA (activated as a 1 mg/ml stock for 10 minutes in a 0.15% hydrogen peroxide solution), 3.0 micromolar [3H]nicotinamide adenine dinucleotide (470 mci/mmole), 7 micrograms/ml PARP enzyme, and various concentrations of the compounds to be tested. The reaction was initiated by incubating the mixture at 25° C. After 15 minutes' incubation, the reaction was terminated by adding 500 microliters of ice cold 20% (w/v) trichloroacetic acid. The precipitate formed was transferred onto a glass fiber filter (Packard Unifilter-GF/B) and washed three times with ethanol. After the filter was dried, the radioactivity is determined by scintillation counting.

The compounds of this invention were found to have potent enzymatic activity in the range of a few $\mu M$ to 20 M in $IC_{50}$ in this inhibition assay. The $IC_{50}$ data for the following compounds are shown below in TABLE VII.

TABLE VII

| Compound | Approximate $IC_{50}$'s |
|---|---|
| (isoquinolinone with $NO_2$ substituent) | 5 $\mu M$ |
| (isoquinolinone with phenyl substituent) | 30 $\mu M$ |
| (isoquinolinone with COOH substituent) | 10 $\mu M$ |

TABLE VII-continued

| Compound | Approximate IC$_{50}$'s |
|---|---|
| 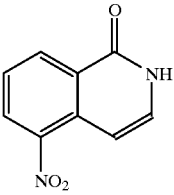 | 10 μM |
| 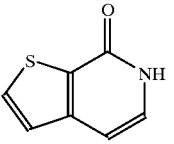 | 50 μM |
| 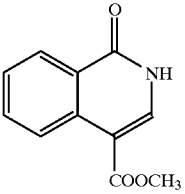 | 0.8 μM |
| 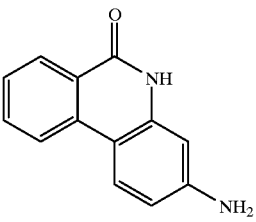 | 4 μM |
| 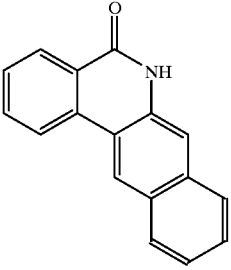 | 100 μM |
| 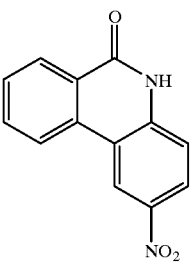 | 0.9 μM |

TABLE VII-continued

| Compound | Approximate IC$_{50}$'s |
|---|---|
| 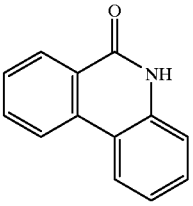 | 5.2 μM |
| 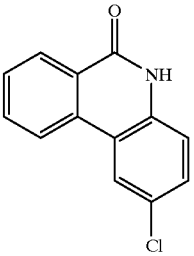 | 0.7 μM |
| 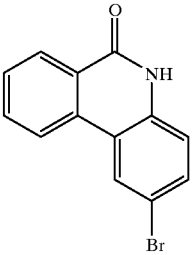 | 1.1 μM |
| 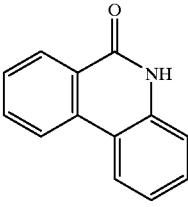 | 0.2 μM |

EXAMPLE 2

Neuroprotective Effects on Focal Cerebral Ischemia in Rats

Focal cerebral ischemia experiments are performed using male Wistar rats weighing about 250–300 g, which were anesthetized with 4% halothane. Anesthesia is maintained with 1.0–1.5% halothane until the end of surgery. The animals are installed in a warm environment to avoid a decrease in body temperature during surgery.

An anterior midline cervical incision is made. The right common carotid artery (CCA) is exoosed and isolated from the vagus nerve. A silk suture is placed and tied around the CCA in proximity to the heart. The external carotid artery (ECA) is then exposed and ligated with a silk suture. A puncture is made in the CCA, and a small catheter (PE 10, Ulrich & Co., St-Gallen, Switzerland) is gently advanced to the lumen of the internal carotid artery (ICA). The pterygopalatine artery is not occluded. The catheter is tied in place with a silk suture.

Then, a 4-0 nylon suture (Brau-Medical, Crissier, Switzerland) is introduced into the catheter lumen and pushed until the tip blocks the anterior cerebral artery. The length of catheter into the ICA is approximately 19 mm from the origin of the ECA. The suture is maintained in this position by occlusion of the catheter with heat. One cm of catheter and nylon suture are left protruding so that the suture could be withdraw to allow reperfusion. The skin incision is then closed with wound clips.

The animals are maintained in a warm environment during recovery from anesthesia. Two hours later, the animals are re-anesthetized, the clips are discarded, and the wound is re-opened. The catheter is cut, and the suture is pulled out. The catheter is then obturated again with heat, and wound clips are placed on the wound. The animals are allowed to survive for 24 hours with free access to food and water. The rats are then sacrificed with $CO_2$ and decapitated.

The brains are immediately removed, frozen on dry ice and stored at $-80°$ C. The brains are then cut in 0.02 mm-thick sections in a cryocut at $-190°$ C., selecting one of every 20 sections for further examination. The sections are stained with cresyl violet according to the Nissl procedure. Each stained section is examined under a light microscope, and the regional infarct area is determined according to the presence of cells with morphological changes.

Various doses of compounds of the invention are tested in this model. The compounds are given either intravenously or intraperitoneally, as a single dose or as a series of multiple doses, and are given at different times, both before or after the onset of ischemia. It is expected by the inventors that the compounds of the invention would provide protection from ischemia in the range of about 20 to 80 per cent.

EXAMPLE 3

Neuroprotective Effects on Focal Cerebral Ischemia in Rats

Female Sprague-Dawley rats, each weighing about 300–350 g, are anesthetized with intraperitoneal ketamine at a dose of 150 mg/kg. The rats are endotracheally intubated and ventilated with oxygen-enriched room air using a Harvard rodent ventilator. Polyethylene catheters inserted into the carotid artery and into the femoral vein are used for monitoring artery blood pressure and fluid administration respectively. Arterial $pCO_2$ is maintained between about 35 and 45 mm Hg by adjusting the respirator rate.

The rat chests are opened by median sternotomy, the pericardium is incised, and the hearts are cradled with a latex membrane tent. Hemodynamic data are obtained at baseline after at least a 15-minute stabilization period following the end of the surgical operation. The LAD (left anterior descending) coronary artery is ligated for 40 minutes, and then re-perfused for 120 minutes. After the 120-minute reperfusion, the LAD artery is re-occluded, and a 0.1 ml bolus of monastral blue dye is injected into the left atrium to determine the ischemic risk region.

The hearts are then arrested with potassium chloride and cut into five 2–3 mm thick transverses ices. Each slice is weighed and incubated in a 1% solution of triphenyltetrazolium chloride to visualize the infarcted myocardium located within the risk region. Infarct size is calculated by summing the values for each left ventricular slice and is further expressed as a fraction of the risk region of the left ventricle.

Various doses of the compounds of the invention are tested in this model. The compounds are given either intravenously or intraperitoneally, in a single dose or as a series of multiple doses, and are given at different times, both before or after the onset of ischemia. It is expected by the inventors that the compounds of the invention would provide protection against ischemia/reperfusion injury in the range of about 16 to 40 per cent.

EXAMPLE 4

Neuroprotective Effects on Focal Cerebral Ischemia in Rats

Focal cerebral ischemia was produced by cauterization of the right distal MCA (middle cerebral artery) with bilateral temporary common carotid artery occlusion in male Long-Evans rats for 90 minutes. All procedures performed on the animals were approved by the University Institutional Animal Care and Use Committee of the University of Pennsylvania. A total of 42 rats (weights: 230–340 g) obtained from Charles River were used in this study. The animals fasted overnight with free access to water prior to the surgical procedure.

Two hours prior to MCA occlusion, varying amounts (control, n=14; 5 mg/kg, n=7; 10 mg/kg, n=7; 20 mg/kg, n=7; and 40 mg/kg, n=7) of the PARP inhibitor compound, 3,4-dihydro-5-[4-(1-piperidinyl)-butoxy]-1(2H)-isoquinolinone ("DPQ"), were dissolved in dimethyl sulfoxide (DMSO) using a sonicator. A volume of 1.28 ml/kg of the resulting solution was injected intraperitoneally into fourteen rats.

The rats were then anesthetized with halothane (4% for induction and 0.8%–1.2% for the surgical procedure) in a mixture of 70% nitrous oxide and 30% oxygen. The body temperature was monitored by a rectal probe and maintained at 37.5±0.5° C. with a heating blanket regulated by a homeothermic blanket control unit (Harvard Apparatus Limited, Kent, U.K.). A catheter (PE-50) was placed into the tail artery, and arterial pressure was continuously monitored and recorded on a Grass polygraph recorder (Model 7D, Grass Instruments, Quincy, Mass.). Samples for blood gas analysis (arterial pH, $PaO_2$ and $PaCO_2$) were also taken from the tail artery catheter and measured with a blood gas analyzer (ABL 30, Radiometer, Copenhagen, Denmark). Arterial blood samples were obtained 30 minutes after MCA occlusion.

The head of the animal was positioned in a stereotaxic frame, and a right parietal incision between the right lateral canthus and the external auditory meatus was made. Using a dental drill constantly cooled with saline, a 3 mm burr hole was prepared over the cortex supplied by the right MCA, 4 mm lateral to the sagittal suture and 5 mm caudal to the coronal suture. The dura mater and a thin inner bone layer were kept, care being taken to position the probe over a tissue area devoid of large blood vessels. The flow probe (tip diameter of 1 mm, fiber separation of 0.25 mm) was lowered to the bottom of the cranial burr hole using a micromanipulator. The probe was held stationary by a probe holder secured to the skull with dental cement. The microvascular blood flow in the right parietal cortex was continuously monitored with a laser Doppler flowmeter (FloLab, Moor, Devon, U.K., and Periflux 4001, Perimed, Stockholm, Sweden).

Focal cerebral ischemia was produced by cauterization of the distal portion of the right MCA with bilateral temporary common carotid artery (CCA) occlusion by the procedure of Chen et al., "A Model of Focal Ischemic Stroke in the Rat: Reproducible Extensive Cortical Infarction", *Stroke*, 17:738–43 (1986) and/or Liu et al., "Polyethylene Glycol-conjugated Superoxide Dismutase and Catalase Reduce Ischemic Brain Injury", *Am. J. Physiol.*, 256:H589–93 (1989), both of which are hereby incorporated by reference.

Specifically, bilateral CCA's were isolated, and loops made from polyethylene (PE-10) catheter were carefully passed around the CCA's for later remote occlusion. The incision made previously for placement of the laser doppler probe was extended to allow observation of the rostral end of the zygomatic arch at the fusion point using a dental drill, and the dura mater overlying the MCA was cut. The MCA distal to its crossing with the inferior cerebral vein was lifted by a fine stainless steel hook attached to a micromanipulator and, following bilateral CCA occlusion, the MCA was cauterized with an electrocoagulator. The burr hole was covered with a small piece of Gelform, and the wound was sutured to maintain the brain temperature within the normal or near-normal range.

After 90 minutes of occlusion, the carotid loops were released, the tail arterial catheter was removed, and all of the wounds were sutured. Gentamicin sulfate (10 mg/ml) was topically applied to the wounds to prevent infection. The anesthetic was discontinued, and the animal was returned to his cage after awakening. Water and food were allowed ad libitum.

Two hours after MCA occlusion, the animals were given the same doses of the PARP inhibitor as in the pre-treatment. Twenty-four hours after MCA occlusion, the rats were sacrificed with an intraperitoneal injection of pentobarbital sodium (150 mg/kg). The brain was carefully removed from the skull and cooled in ice-cold artificial CSF for five minutes. The cooled brain was then sectioned in the coronal plane at 2 mm intervals using a rodent brain matrix (RBM-4000C, ASI Instruments, Warren, Mich.). The brain slices were incubated in phosphate-buffered saline containing 2% 2,3,5-triphenyltetrazolium chloride (TTC) at 370° C. for ten minutes. Color photographs were taken of the posterior surface of the stained slices and were used to determine the damaged area at each cross-sectional level using a computer-based image analyzer (NIH Image 1.59). To avoid artifacts due to edema, the damaged area was calculated by subtracting the area of the normal tissue in the hemisphere ipsilateral to the stroke from the area of the hemisphere contralateral to the stroke, by the method of Swanson et al., "A Semiautomated Method for Measuring Brain Infarct Volume", *J. Cereb. Blood Flow Metabol.*, 10:290–93 (1990), the disclosure of which is hereby incorporated by reference. The total volume of infarction was calculated by summation of the damaged volume of the brain slices.

The cauterization of the distal portion of the right MCA with bilateral temporary CCA occlusion consistently produced a well-recognized cortical infarct in the right MCA territory of each test animal. There was an apparent uniformity in the distribution of the damaged area as measured by TTC staining in each group, as shown in FIG. 1.

In FIG. 1, the distribution of the cross-sectional infarct area at representative levels along the rostrocaudal axis was measured from the interaural line in non-treated animals and in animals treated with 10 mg/kg of 3,4-dihydro-5-[4-(1-piperidinyl)-butoxy]-1(2H)-isoquinolinone. The area of damage was expressed as mean±standard deviation. Significant differences between the 10 mg-treated group and the control group were indicated (*p<0.02, p<0.01, p<0.001). The 5 mg/kg and 20 mg/kg curves fell approximately halfway between the control and the 10 mg/kg curves, whereas the 40 mg/kg curve was close to the control. The 5, 20 and 40 mg/kg curves were omitted for clarity.

PARP inhibition led to a significant decrease in the damaged volume in the 5 mg/kg-treated group (106.7±23.2 mm$^3$, p<0.001), the 10 mg/kg-treated group (76.4±16.8 mm$^3$, p<0.001), and the 20 mg/kg-treated group (110.2±42.0 mm$^3$, p<0.01), compared to the control group (165.2±34.0 mm$^3$. The data are expressed as mean±standard deviation. The significance of differences between groups was determined using an analysis of variance (ANOVA) followed by Student's t-test for individual comparisons.

There was no significant difference between the control and the 40 mg/kg-treated group (135.6±44.8 mm$^3$). However, there were significant differences between the 5 mg/kg-treated group and the 10 mg/kg-treated group (p<0.02), and between the 10 mg/kg-treated group and the 40 mg/kg-treated group (p<0.01), as shown in FIG. 2.

Figure 2:
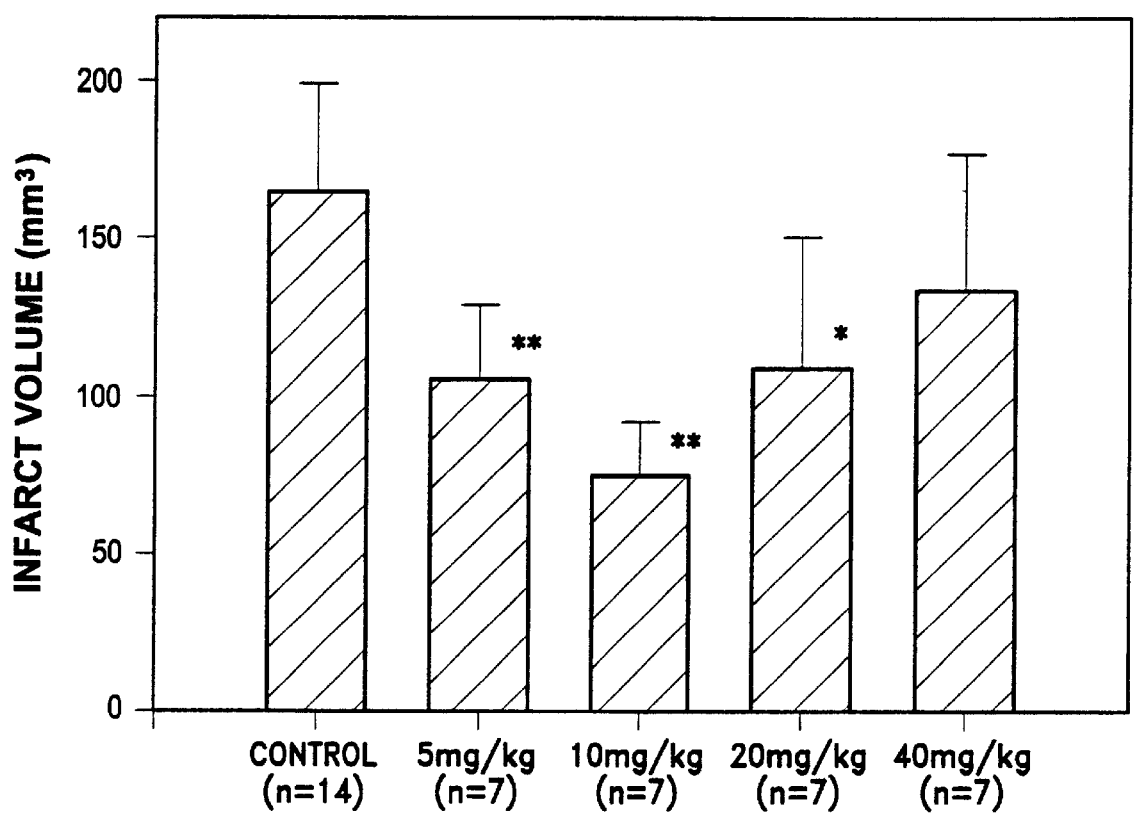
FIG. 2 shows the effect of intraperitoneal administration of 3,4-dihydro-5-[4-(1-piperidinyl)-butoxy]-1(2H)-isoquinolinone on the infarct volume.

In FIG. 2, the effect of intraperitoneal administration of 3,4-dihydro-5-[4-(1-piperidinyl)-butoxy]-1(2H)-isoquinolinone on the infarct volume was depicted graphically. The volumes of infarct were expressed as mean±standard deviation. Significant differences between the treated groups and the control group were indicated (*p<0.01, **p<0.001). It is not clear why a high dose (40 mg/kg) of the PARP inhibitor, 3,4-dihydro-5-[4-(1-piperidinyl)-butoxy]-1(2H)-isoquinolinone, was less neuroprotective. The U-shaped dose-response curve may suggest dual effects of the compound.

However, overall, the in vivo administration of the inhibitor led to a substantial reduction in infarct volume in the focal cerebral ischemia model in the rat. This result indicated that the activation of PARP plays an important role in the pathogenesis of brain damage in cerebral ischemia.

The values of arterial blood gases ($PaO_2$, $PaCO_2$ and pH) were within the physiological range in the control and treated groups with no significant differences in these parameters among the five groups, as shown below in Table VIII. A "steady state" MABP was taken following completion of the surgical preparation, just prior to occlusion; an "ischemia" MABP was taken as the average MABP during occlusion.

TABLE VIII

| | $PaO_2$ (mm Hg) | $PaCO_2$ (mm Hg) | pH | MABP (mm Hg) Steady State | Ischemia |
|---|---|---|---|---|---|
| Control group (n = 4) | 125 ± 21 | 38.6 ± 4.6 | 7.33 ± 0.05 | 79 ± 14 | 91 ± 13** |
| 5 mg/kg-treated group (n = 7) | 126 ± 20 | 38.0 ± 2.8 | 7.36 ± 0.02 | 78 ± 5 | 91 ± 12** |
| 10 mg/kg-treated group (n = 7) | 125 ± 16 | 39.3 ± 5.2 | 7.34 ± 0.03 | 80 ± 9 | 90 ± 14* |
| 20 mg/kg-treated group (n = 7) | 122 ± 14 | 41.3 ± 2.8 | 7.35 ± 0.23 | 79 ± 10 | 91 ± 12** |
| 40 mg/kg-treated group (n = 7) | 137 ± 17 | 39.5 ± 4.7 | 7.33 ± 0.24 | 78 ± 4 | 88 ± 12* |

\* = Significantly different from the steady state value, p < 0.05.
\*\* = Significantly different from the steady state value, p < 0.01.

There were no significant differences in any physiological parameter, including mean arterial blood pressure (MABP), prior to MCA and CCA occlusion among the five groups. Although MABP was significantly elevated following occlusion in all five groups, there were no significant differences in MABP during the occlusion period among the groups.

Since the blood flow values obtained from the laser doppler were in arbitrary units, only percent changes from the baseline (prior to occlusion) were reported. Right MCA and bilateral CCA occlusion produced a significant decrease in relative blood flow in the right parietal cortex to 20.8±7.7% of the baseline in the control group (n=5), 18.7±7.4% in the 5 mg/kg-treated group (n=7), 21.4±7.7% in the 10 mg/kg-treated group (n=7) and 19.3±11.2% in the 40 mg/kg-treated group (n=7). There were no significant differences in the blood flow response to occlusion among the four groups. In addition, blood flow showed no significant changes throughout the entire occlusion period in any group.

Following release of the carotid occlusions, a good recovery of blood flow (sometimes hyperemia) was observed in the right MCA territory of all animals. Reperfusion of the ischemic tissue resulted in the formation of NO and peroxynitrite, in addition to oxygen-derived free radicals. All of these radicals have been shown to cause DNA strand breaks and to activate PARP.

EXAMPLE 5

A patient has just been diagnosed with acute vascular stroke and is immediately administered a compound of formula I, either as a single dose or as a series of divided doses of the compound. After this initial treatment and, depending upon the patient's neurological symptoms, the patient may receive another dose of the same or a different compound of the invention in parenteral form, such as by intermittent or continuous intravenous infusion, or in the form of a capsule or tablet. It is expected by the inventors that further neural tissue damage would be prevented to a significant degree, that the patient's neurological symptoms would considerably lessen, and that there would be fewer residual neurological effects post-stroke. In addition, it is expected by the inventors that the re-occurrence of vascular stroke would be reduced or prevented.

EXAMPLE 6

A patient has just been diagnosed with acute multiple vascular strokes and is comatose. Immediately, a physician or a nurse parenterally administers a single dose or a series of divided doses of a compound of formula I. Due to the comatose state of the patient, the patient will receive the same or a different compound by intermittent or continuous administration via implantation of a biocompatible, biodegradable polymeric matrix delivery system comprising the compound. A subdural pump could also be inserted to provide for administration of the compound directly to the infarct area of the brain. It is expected by the inventors that the patient would awaken from the coma more quickly than if the compound of the invention had not been administered. The treatment is also expected to reduce the severity of the patient's residual neurological symptoms. In addition, the inventors expect that reoccurence of vascular stroke would be reduced for this patient.

EXAMPLE 7

A patient is diagnosed with life-threatening cardiomyopathy and requires a heart transplant. Until a donor heart is found, the patient is maintained on Extra Corporeal Oxygenation Monitoring (ECMO). A donor heart is located, and the patient undergoes a transplant procedure in which the patient is placed on a heart-lung pump during the surgical procedure. The patient receives a pharmaceutical composition containing a compound of formula I intracardiac within a specified period of time prior to the re-routing of the patient's circulation from the heart-lung pump to his or her own new heart, thus preventing cardiac reperfusion injury when the patient's new heart starts pumping to circulate the patient's blood.

EXAMPLE 8

Before undergoing radiation therapy to treat cancer, a patient may be administered an effective amount of a compound or a pharmaceutical composition of the present invention. It is expected that the compound or pharmaceutical composition would act as a radiosensitizer and make the tumor more susceptible to radiation therapy.

The invention being thus described, it will be obvious that the same may be varied in many ways. Such variations are not to be regarded as a departure from the spirit and scope of the invention, and all such modifications are intended to be included within the scope of the following claims.

We claim:

1. A compound of formula II:

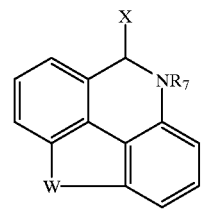

or a pharmaceutically acceptable base or acid addition salt, wherein X is double bonded oxygen or —OH;

$R_7$ is hydrogen or lower alkyl;

W is —O—, —S—, —$NR^1$—, wherein $R^1$ is hydrogen or lower alkyl; and at least one of the benzene rings is optionally substituted with at least one substituent selected from the group consisting of a straight chain alkyl group, a branched chain alkyl group, a straight chain alkenyl group, a branched chain alkenyl group, a straight chain alkynyl group, a branched chain alkynyl group, a cycloakenyl group, an aralkyl group, an aryl group, an alkoxy group, an aralkyloxy group, an alkanoyl group, a haloalkyl group, a non-aromatic heterocyclic group, a hydroxy, a carboxy, a carbonyl, an amino, an alkylamino, an amido, a cyano, an isocyano, a nitro, a nitroso, a nitrilo, an isonitrilo, an imino, an azo, a diazo, a sulfonyl, a sulfoxy, a thio, a thiocarbonyl, a cycloalkyl, an alkenoxy, an aryloxy, a sulfhydryl and a halo.

2. A compound of claim 1 wherein said at least one substituent is selected from the group consisting of methyl, ethyl, propyl, butyl, pentyl, hexyl, isopropyl, isopropyl, isobutyl, tert-butyl, n-pentyl, 2-methylpentyl, 2-methylhexyl, dodecyl, octadecyl, ethenyl, propenyl, butenyl, pentenyl, 2-methylpentenyl, vinyl, isopropenyl, 2,2-dimethyl-1-propenyl, decenyl, hexadecenyl, ethynyl, propynyl, butynyl, pentynyl, hexynyl, heptynyl, octynyl, cyclobutyl, cyclopentyl, cyclohexyl, cycloheptyl, cyclooctyl, cyclononyl, cyclodecyl, cyclopropenyl, cyclopentadienyl, cyclohexenyl, cyclooctenyl, benzyl, 3-(1)-naphthyl-1-propyl, p-halobenzyl, p-ethylbenzyl, 1-phenyl-1-propyl, 3-pyridinyl-1-propyl, 1-phenyl-2-sec-butyl, 4-phenyl-4-methyl-1-pentyl, phenyl, naphthyl, indenyl, azulenyl, fluorenyl, anthracenyl, indolyl, isoindolyl, indolinyl, benzofuranyl, benzothiophenyl, indazolyl, benzamidazolyl, benzathiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quionolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, methoxy, ethoxy, sec-propoxy, tert-butoxy, pentoxy, nonoxy, ethenoxy, 2-propenoxy, 3-butenoxy, 2,2-dimethyl-3-butenoxy, 1-hexenoxy, 3-octenoxy, 2-nonenoxy, phenoxy, naphthoxy, pyridinoxy, benzylocy, 1-naphthyl-2-ethoxy, formyl, acetyl, propanoyl, butanoyl, pentanoyl, benzoyl, trifluoromethyl, a non-aromatic heterocyclic group, hydroxy, carboxy, carbonyl, amino, alklyamino, amido, cyano, isocyano, nitro, nitroso, nitrilo, isonitriolo, imino, azo, diazo, sulfonyl, sulfoxy, $SO_3K$, thio, thiocarbonyl, alklythio, sulfhydryl and halo.

3. A compound according to claim 1 wherein at least one of the benzene rings of formula II is substituted with at least one of said substituents.

4. A compound according to claim 1 wherein one of the benzene rings of formula II is substituted with at least one of said substituents.

5. A compound of claim 1 wherein one of the benzene rings of formula II is substituted by a piperidine, a piperazine, an imidazolidine or a hydroxy.

6. A compound according to claim 2 wherein $R_7$ is hydrogen.

7. A compound according to claim 6 wherein X is double bonded oxygen.

8. A pharmaceutical composition comprising at least one compound according to claim 1 and a pharmaceutically acceptable diluent.

9. The composition of claim 8 wherein said compound has an $IC_{50}$ for inhibiting poly(ADP-ribose)polymerase in vitro of 100 μM or less.

10. The composition of claim 9 wherein said compound has an $IC_{50}$ of 25 μM or less.

11. A composition according to claim 8 wherein said composition is in the form of a capsule, tablet, suspension, emulsion or solid implant.

12. A method of inhibiting poly(ADP-ribose)polymerase activity comprising administering a compound of claim 1 to a mammal.

13. A method of treating neural tissue damage resulting from cerebral ischemia or reperfusion injury comprising administering a compound according to claim 1 to a mammal.

14. The method of claim 13 wherein said mammal is a human.

15. A method of preventing tissue damage resulting from cerebral ischemia or reperfusion injury comprising administering a compound according to claim 1 to a mammal.

16. The method of claim 15 wherein said mammal is a human.

17. A method of treating any one of peripheral neuropathy, traumatic brain injury, physical damage to the spinal chord, stroke, a demyelinating disease or neurological disorder relating to neurodegeneration comprising administering a compound of claim 1 to a person in need of said treatment.

18. The method of treating at least one of Alzheimer's disease, Parkinson's disease, Huntington's disease and amyotrophic lateral sclerosis comprising administering a compound of claim 1 to a person in need of said treatment.

19. A method of treating an inflammatory disorder comprising administering a compound of claim 1 to a person in need of said treatment.

20. A method according to claim 19 wherein said disorder is inflammatory bowel disorder.

21. A method of claim 20 wherein said disorder is Crohn's disease.

22. A method of treating a cardiovascular disorder comprising administering a compound of claim 1 to a person in need of said treatment.

23. A method of claim 22 wherein said cardiovascular disorder is selected from the group consisting of coronary artery disease, angina pectoris, myocardial infarction, cardiogenic shock, and cardiovascular tissue damage.

24. A method of treating septic shock comprising administering a compound of claim 1 to a person in need of said treatment.

25. A method of claim 24 wherein said septic shock is endotoxic shock.

26. A method of treating diabetes comprising administering a compound of claim 1 to a person in need of said treatment.

27. A method of treating arthritis comprising administering a compound of claim 1 to a person in need of said treatment.

28. A method of treating cancer comprising administering a compound a claim 1 to a person in need of said treatment.

29. The method of claim 28, wherein said cancer is selected from the group consisting of: ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovarian (germ cell) cancer, prostate cancer, pancreatic cancer, cancer of the penis, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva and Wilm's tumor.

30. A method of inhibiting poly(ADP-ribose)polymerase activity comprising administering a compound of claim 7 to a mammal.

31. A method of treating neural tissue damage resulting from cerebral ischemia or reperfusion injury comprising administering a compound according to claim 7 to a mammal.

32. The method of claim 31 wherein said mammal is a human.

33. A method of preventing tissue damage resulting from cerebral ischemia or reperfusion injury comprising administering a compound according to claim 7 to a mammal.

34. The method of claim 33 wherein said mammal is a human.

35. A method of treating any one of peripheral neuropathy, traumatic brain injury, physical damage to the spinal chord, stroke, a demyelinating disease or neurological disorder relating to neurodegeneration comprising administering a compound of claim 7 to a person in need of said treatment.

36. The method of treating at least one of Alzheimer's disease, Parkinson's disease, Huntington's disease and amyotrophic lateral sclerosis comprising administering a compound of claim 7 to a person in need of said treatment.

37. A method of treating an inflammatory disorder comprising administering a compound of claim 7 to a person in need of said treatment.

38. A method according to claim 37 wherein said disorder is inflammatory bowel disorder.

39. A method of claim 38 wherein said disorder is Crohn's disease.

40. A method of treating a cardiovascular disorder comprising administering a compound of claim 7 to a person in need of said treatment.

41. A method of claim 40 wherein said cardiovascular disorder is selected from the group consisting of coronary artery disease, angina pectoris, amyocardial infarction, cardiogenic shock, and cardiovascular tissue damage.

42. A method of treating septic shock comprising administering a compound of claim 7 to a person in need of said treatment.

43. A method of claim 42 wherein said septic shock is endotoxic shock.

44. A method of treating diabetes comprising administering a compound of claim 7 to a person in need of said treatment.

45. A method of treating arthritis comprising administering a compound of claim 7 to a person in need of said treatment.

46. A method of treating cancer comprising administering a compound a claim 7 to a person in need of said treatment.

47. The method of claim 46, wherein said cancer is selected from the group consisting of: ACTH-producing tumors, acute lymphocytic leukemia, acute nonlymphocytic leukemia, cancer of the adrenal cortex, bladder cancer, brain cancer, breast cancer, cervic cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, prostate cancer, pancreatic cancer, penis cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva and Wilm's tumor.

* * * * *